(12) United States Patent
Nguyen-Demary et al.

(10) Patent No.: US 9,943,436 B2
(45) Date of Patent: Apr. 17, 2018

(54) CONTROLLED DISCHARGE OSTOMY APPLIANCE AND SHIELD THEREFOR

(71) Applicant: CONVATEC TECHNOLOGIES INC., Las Vegas, NV (US)

(72) Inventors: Tinh Nguyen-Demary, Miltown, NJ (US); John Cline, New Brunswick, NJ (US); John Blum, Toms River, NJ (US); Gary Stacey, Cambridge (GB); Philip Davies, Solihull (GB); Trevor Beckett, Cambridge (GB)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 771 days.

(21) Appl. No.: 14/466,785

(22) Filed: Aug. 22, 2014

(65) Prior Publication Data

US 2014/0364823 A1    Dec. 11, 2014

Related U.S. Application Data

(62) Division of application No. 13/395,047, filed as application No. PCT/US2010/048211 on Sep. 9, 2010, now Pat. No. 8,845,606.

(Continued)

(51) Int. Cl.
*A61F 5/445*    (2006.01)
*A61F 5/448*    (2006.01)
*A61F 5/441*    (2006.01)

(52) U.S. Cl.
CPC .............. *A61F 5/445* (2013.01); *A61F 5/448* (2013.01); *A61F 5/441* (2013.01); *A61F 2005/4486* (2013.01)

(58) Field of Classification Search
CPC combination set(s) only.
See application file for complete search history.

(56) References Cited

U.S. PATENT DOCUMENTS 4,231,369 A    11/1980    Sorensen
4,826,496 A *   5/1989    Ferguson ................ A61F 5/448
                                                604/339

(Continued)

FOREIGN PATENT DOCUMENTS

EP    1348412         10/2003
EP    1774932 A1     4/2007

(Continued)

OTHER PUBLICATIONS

U.S. Appl. No. 13/395,047 Restriction Requirement dated Dec. 6, 2013.

(Continued)

*Primary Examiner* — Tatyana Zalukaeva
*Assistant Examiner* — Guy K Townsend
(74) *Attorney, Agent, or Firm* — Wilson Sonsini Goodrich & Rosati

(57) ABSTRACT

A controlled discharge ostomy appliance assembly comprises (i) a stoma seal that is self-urging with a dynamic damping characteristic that resists changes of seal volume, (ii) a press-fit coupling member displaceable from an unlocked position to a locked position as part of a press-fit process, and (iii) a single-use frangible portion. The assembly further includes a protector shield removably fastened to the appliance forming a combined assembly therewith. The protector shield comprises (i) a seal displacer manipulable for displacing the stoma seal to a non-operative position ready for fitting, (ii) a substantially rigid coupling member guard portion for protecting the state of the coupling member, and (iii) a bracing portion for bracing the single-use frangible portion.

12 Claims, 12 Drawing Sheets

Related U.S. Application Data

(60) Provisional application No. 61/276,352, filed on Sep. 11, 2009.

(56) References Cited

U.S. PATENT DOCUMENTS

| | | | |
|---|---|---|---|
| 4,846,820 A | | 7/1989 | Jensen |
| 4,889,534 A | | 12/1989 | Mohiuddin et al. |
| 4,950,223 A | * | 8/1990 | Silvanov ............... A61F 5/441 |
| | | | 128/DIG. 25 |
| 5,496,296 A | | 3/1996 | Holmberg |
| 5,730,735 A | * | 3/1998 | Holmberg ............... A61F 5/448 |
| | | | 604/338 |
| 6,071,268 A | * | 6/2000 | Wagner ................... A61F 5/443 |
| | | | 604/332 |
| 6,210,384 B1 | * | 4/2001 | Cline ...................... A61F 5/448 |
| | | | 604/338 |
| 6,723,079 B2 | | 4/2004 | Cline |
| 7,347,844 B2 | | 3/2008 | Cline et al. |
| 7,857,796 B2 | | 12/2010 | Cline et al. |
| 8,460,259 B2 | | 6/2013 | Tsai |
| 8,845,606 B2 | * | 9/2014 | Nguyen-Demary .... A61F 5/448 |
| | | | 604/333 |
| 2002/0104770 A1 | | 8/2002 | Shapeton et al. |
| 2003/0187393 A1 | * | 10/2003 | Cline ...................... A61F 5/445 |
| | | | 604/131 |
| 2004/0181197 A1 | * | 9/2004 | Cline ...................... A61F 5/445 |
| | | | 604/337 |
| 2006/0206069 A1 | | 9/2006 | Cline |
| 2007/0088300 A1 | | 4/2007 | Cline et al. |
| 2007/0100303 A1 | | 5/2007 | Gregory et al. |
| 2007/0123832 A1 | | 5/2007 | Cline et al. |
| 2007/0129695 A1 | | 6/2007 | Blum |
| 2011/0040269 A1 | | 2/2011 | Cline |
| 2012/0179124 A1 | | 7/2012 | Nguyen-Demary |
| 2014/0364823 A1 | * | 12/2014 | Nguyen-Demary .... A61F 5/445 |
| | | | 604/333 |

FOREIGN PATENT DOCUMENTS

| | | |
|---|---|---|
| EP | 1795157 A2 | 6/2007 |
| EP | 2185110 A1 | 5/2010 |
| JP | 2007105475 A | 4/2007 |
| JP | 2007152123 A | 6/2007 |
| WO | WO 87/06823 | 11/1987 |
| WO | WO 2008/141180 A1 | 11/2008 |
| WO | WO 2009/029610 | 3/2009 |
| WO | WO-2009029610 A1 | 3/2009 |
| WO | WO 2011/031822 A1 | 3/2011 |

OTHER PUBLICATIONS

PCT/US2010/048211 International Preliminary Report on Patentability dated Mar. 13, 2012.
PCT/US2010/048211 Written Opinion dated Dec. 23, 2010.
PCT/US2010/048211 International Search Report dated Jan. 10, 2011.
Canadian Patent Application No. 2,772,527 Official Action dated Jul. 21, 2016.
Korean Patent Application No. 10-2012-7009279 Notice of Preliminary Rejection dated Jan. 18, 2017.
European Patent Application No. 10816058.1 extended European Search Report dated Jul. 6, 2017.
Korean Patent Application No. 10-2017-7007482 Office Action dated Jul. 3, 2017.
Australia Patent Application No. 2016225932 Examination Report No. 1 dated Oct. 25, 2017.

* cited by examiner ary device may, for example, be a shield or packaging
CONTROLLED DISCHARGE OSTOMY APPLIANCE AND SHIELD THEREFOR

CROSS-REFERENCE

This application is a continuation application of U.S. patent application Ser. No. 13/395,047, filed on Mar. 8, 2012, now U.S. Pat. No. 8,845,606, which is a U.S. National Phase of PCT/US10/48211, filed Sep. 9, 2010, which claims the benefit of U.S. Provisional Application No. 61/276,352, filed on Sep. 11, 2009, each of which is entirely incorporated herein by reference.

FIELD OF THE INVENTION

The present invention relates to a controlled discharge ostomy appliance and an auxiliary device therefor. The auxiliary device may, for example, be a shield or packaging for the controlled discharge ostomy appliance.

BACKGROUND TO THE INVENTION

U.S. Pat. No. 6,723,079 and EP-A-1348412 describe controlled discharge ostomy devices including an inflatable membrane seal for creating a temporary conformal closure of the stoma. The inflatable seal comprises a sealed chamber having an inflation port closed by a check valve. After having fitted the appliance at a stoma, the seal is inflated by coupling an external inflation source, for example a pump or a syringe, to the check valve. Once the inflation fluid has been injected into the chamber, the check valve seals the chamber preventing loss of inflation fluid and preserving the inflation state.

Such a system can be comfortable to fit and provide good seal performance, but may require careful design. One design issue is the provision of an external inflation source as a separate item carried by the user, in order to be able to inflate the seal after having fitted the appliance, or to top-up the seal with additional inflation fluid in case of fluid loss or stoma leakage. Another design issue is the importance of keeping the contact pressure between the stoma and the membrane seal in a narrow range, namely as low as possible (to ensure good blood perfusion in the stoma tissue) while maintaining an effective temporary seal against discharge of stool. However, it is difficult to keep the contact pressure in such a narrow range because, for a given amount of inflation fluid in the chamber, any change in chamber volume caused by movement of stoma, directly affects the inflation pressure. During the wear time of an ostomy appliance, the stoma can move dynamically inwardly towards the body and/or outwardly away from the surface of the peristomal skin over a total distance that can exceed 1 cm. This movement can be due to peristaltic motion of the bowel, impending release of stool or gas from the stoma, or muscular contractions of the abdomen. Under conditions when the stoma moves inwardly towards the body (i.e. increasing the volume of the inflation chamber), the contact pressure between the membrane seal and the stoma can fall, increasing the risk of leakage of stool if the contact pressure is too low. In contrast, under conditions when the stoma or its contents pushes outwardly against the membrane seal (reducing the volume of the inflation chamber), contact pressure between the seal and the stoma can potentially rise. During such times, the increased contact pressure may result in undesirable reduced blood perfusion in the stoma. The duration of such conditions may be highly unpredictable, some lasting only seconds, others minutes, and sometimes several hours.

International patent application publication no. WO 2009/029610 describes an alternative seal that is both self-compensating and self-urging towards the stoma. The seal comprises a fluid chamber including a fluid impermeable membrane that forms a movable wall of the fluid chamber, one or more fluid flow regulation ports communicating with the chamber; and resilient foam disposed within the fluid chamber. With such a seal, the contact pressure between the seal and the stoma has both a static component and a dynamic component. The static component comes from the foam, which is compressed by the seal bearing on the stoma, and applies a resilient return force on the stoma. The foam is configured so that the static component of the contact pressure is always within the narrow range of acceptability explained above. The dynamic component of the contact pressure results from the port regulating fluid flow to and from the chamber, as the chamber volume adapts to follow any movement of the stoma. The port defines a dynamic damping characteristic of adaptation of the seal, in addition to the effect of the foam.

Such a self-urging design has the potential advantage that no external inflation source is needed, thereby avoiding the user having to carry such a separate device. The pressure inside the seal is self-regulating, and the seal can adapt to different volumes automatically. While the foam permits a wide range of stoma shapes and sizes to be accommodated, the dynamic damping characteristic resists compression of the seal should the stoma begin to push outwardly. The fluid trapped in the chamber by the damping characteristic generates a temporary, dynamic increase in the contact pressure exerted by the seal to counter such a challenge from the stoma. A transient challenge may be caused by stool and flatus in the stoma, and the temporary increase in sealing pressure enhances the seal against escape of stool, without the increased sealing pressure being exerted for too long to obstruct regular blood perfusion of the stoma. The damping characteristic only temporarily traps inflation fluid, thereby allowing the seal to adapt in volume if the outward movement of the stoma is more than transient.

US-A-2007/088300 describes a single-use ostomy appliance including an ostomy coupling for releasably coupling first and second portions at a stomal orifice. The two portions may be separable body-side and non-body-side parts, or the two portions may be portions of a unitary ostomy device such as a controlled evacuation device. The coupling includes a mechanical fastener configured such that the coupling is rendered substantially not resecurable after the fastener is released.

US-A-2007/129695 describes an ostomy coupling including a body-side coupling member, an appliance-side coupling member including plural fastener lugs, and a bracing member. The lugs flex independently of each other to provide plural independent latching fastenings. The bracing member is moved between a bracing position in which the bracing member locks the lugs by resisting flexing movement, and a non-bracing or dis-mounted position in which the lugs are free to flex. The ostomy coupling is used with an ostomy pouch or with a controlled discharge ostomy appliance.

The present invention seeks to further enhance versatility and ease of use of controlled discharge ostomy appliances.

SUMMARY OF THE PRESENT INVENTION

Aspects of the invention are defined in the claims.

Broadly speaking, a first aspect of the present invention is based on a surprising appreciation that the desirable damping characteristic of the self-urging seal described above, becomes an unwanted hindrance when fitting the appliance to a stoma. The natural shape of the self-urging seal when not in contact with the stoma is a fully distended form, projecting significantly more than the shape when in contact with a stoma. During the fitting process, as the appliance is pressed towards the skin, the seal contacts the stoma and compresses dynamically, and significantly in volume, to conform to the stoma shape. The problem is that the damping characteristic is designed specifically to resist such dynamic compression of the seal, and instead to generate a counter force pressing on the stoma. This can result in three issues:

(i) the resistance to dynamic compression results in an initially high contact pressure against the stoma, which can be significantly higher than that normally expected when in an operative state. The high contact pressure makes fitting uncomfortable, and the discomfort can last beyond the fitting stage until sufficient time has passed for the dynamic damping effect to have eased, and pressure balance to be achieved;

(ii) the final shape adopted by the seal might not be that matching a natural shape of the stoma, because both the seal and the stoma are subjected to the high contact pressure. This may reduce the efficacy of the seal; and (iii) the reaction force in the seal is in turn supported through an adhesive attachment between the appliance and the skin. The greater contact pressure on the stoma results in a greater reaction force, placing additional stress on the adhesive attachment, which can be greater than that normally encountered once in the operative state. The additional stress may risk weakening the adhesive attachment, or increase the risk of leakage. With the appliance in place, it is difficult if not impossible to observe or verify the state of the adhesive attachment, and so this problem may go unnoticed.

The above issues may be mitigated by reducing the damping characteristic of the seal to allow the seal to change shape more readily. However, reducing the damping characteristic is undesirable, because the seal then has less ability to resist an outward challenge from the stoma. Thus we have discovered that there is an inherent incompatibility between a desirably high damping characteristic that enhances dynamic seal performance in use, and a requirement for a small damping characteristic to facilitate initial fitting of the appliance at a stoma.

The first aspect of the invention provides a different approach for a controlled discharge ostomy appliance including a self-urging seal. As used herein, a self-urging seal means, for example, a seal that does not require an external source, such as an inflation pump or syringe, to generate a sealing force or urging force towards the stoma. The self-urging seal may optionally include a resilient component (e.g. a resilient device or member) for generating a sealing or urging force, and/or a damping device for damping displacement of the seal in addition to the effect of the resilient member. The invention involves placing the seal in (or displacing the seal to) a non-deployed state prior to fitting the appliance. Displacing the seal against the urging force prior to fitting avoids the stoma being subjected to the seal's resistance to compression at the time of fitting. In the non-deployed state there is substantially no contact between the seal and stoma (or at least less contact compared to a fully deployed state of the seal). Once released, the seal begins to deploy automatically under the seal's own self-urging effect.

If the self-urging seal has a dynamic damping characteristic, not only does the above technique avoid high contact pressure being exerted on the stoma during fitting, but the initial contact pressure can be even smaller than would be exerted by the resilient member alone. This is because the damping characteristic may also act in reverse, damping or slowing movement of the seal from the non-deployed state towards the stoma. The full force from the resilient foam is only exerted when the seal has deployed and reaches pressure balance.

In addition to more comfortable fitting, deploying the seal into contact with the stoma from a non-deployed condition may achieve a better fitting shape of the seal, than if the seal is forced to compress when fitted in a fully-deployed condition. It is believed that this better fitting shape may be a result of (i) the seal being able to drape around the stoma more freely as contacts the stoma progressively during deployment, and/or (ii) avoiding or reducing the extent to which the stoma is itself deformed from its natural shape by contact pressure on the stoma.

The seal may be placed in the non-deployed state at any time between, and inclusive of, manufacture and immediately prior to fitting of the appliance. In one form, it is preferred that the seal be displaceable to the non-deployed state by a user at a time chosen by a user, for example, shortly before fitting.

A seal displacer is coupled releasably (or coupleable releasably) to the appliance. For example, the seal displacer is coupled by means of a mechanical or adhesive fastener, to form a combined assembly with the appliance. The fastener may interlock with, or otherwise attach to, an ostomy coupling member of the appliance intended for mounting the appliance in an operative position at a stoma. Alternatively, the fastener may interlock with, or otherwise attach to, a portion of the appliance distinct from the ostomy coupling member. The portion of the appliance may, for example, be a periphery of a housing or cover of the appliance. Avoiding attachment to and/or contact with the ostomy coupling member preserves the state of the ostomy coupling member until first use.

In a preferred form, the seal displacer is manipulable by a user to displace the seal to the non-deployed position at a time chosen by the user. The seal displacer may be comprised in an auxiliary device for the appliance. The auxiliary device may, for example, be in the form of a protector or shield or other packaging for the appliance. Use of the seal displacer enables the seal to be manipulated with the protector still assembled to the appliance, thereby avoiding risk of soiling or damaging the seal surface. The seal displacer is releasable from the appliance, whereupon the seal begins to deploy under the seal's self-urging effect.

The seal displacer is preferably displaceable between a first limit position, in which the seal displacer accommodates the seal in a (at least near) fully deployed shape to which the seal distends naturally, and a second limit position corresponding to the non-deployed state of the seal. The first limit position may optionally define a cup shape for receiving the seal, and/or the second limit position may optionally define a counter-cup shape with an opposite convexity to the first limit position. Additionally or alternatively, the seal displacer may be configured to be generally bistable, adopting stably either one of the limit positions.

The seal displacer may be configured to cover substantially all, or at least a majority of, the otherwise exposed surface of the seal. The seal displacer may extend across the otherwise exposed surface, from one peripheral portion of the seal to an opposite peripheral portion.

The seal preferably has a damping characteristic such that the seal deploys progressively from the non-deployed state once released. The deployment interval (the time taken to deploy from the non-deployed state to a full deployed state) may be at least 1 minute, or at least 2 minutes, or at least 3 minutes, or at least 4 minutes, or at least 5 minutes, or at least 10 minutes. The deployment interval is preferably sufficient to provide the user with sufficient time to fit the appliance at the stoma, before the seal deploys significantly towards an operative state. The seal reaches full deployment against the stoma only after fitting of the appliance has been completed, and the appliance is already in its fitted condition.

Broadly speaking, a second aspect of the invention relates to fitting of a controlled discharge ostomy appliance using a separate body fitment worn on the body. The second aspect may provide a controlled discharge ostomy appliance for attachment to a counterpart coupling element. The counterpart coupling element may, for example, be part of an adhesive body-fitment wearable on the body around the stoma. The appliance comprises:

a first member of closed loop form and including a coupling formation for making a press-fit engagement with a said counterpart coupling element when the two are pressed together in a first direction, the coupling formation being deflectable or capable of flexing to permit the press-fit engagement;

a second member having at least one bracing portion;

the first and second members being relatively displaceable in (or generally parallel to) said first direction, from a first unlocked position in which the bracing portion does not substantially brace the coupling formation against said displacement, to a second locked position for (directly or indirectly) bracing the coupling formation of the first member against said displacement;

co-operating retainers on the first and second members for:

(i) retaining said first and second members initially in said unlocked position with a first retention strength until pressure is applied to cause relative displacement of the first and second coupling members to the locked position; and (ii) retaining said first and second members in said locked position with a second retention strength (optionally greater than said first retention strength).

The appliance optionally further includes a single-use feature for obstructing attachment of the device to a said counterpart coupling element more than once. Preferably, the single-use feature comprises a frangible portion of the second member. In order to detach the device after a first use (or first attachment), the frangible portion of the second coupling member is configured to be at least partially torn or broken, thereby releasing the bracing effect of the bracing portion. Thereafter, the second member is substantially incapable of bracing the coupling formation (at least to the same degree as the first attachment).

The counterpart coupling element may be configured such that the assembly force required to press-fit engage with the coupling formation of the first member, is less than the first retention strength.

Prior to first use, the first and second coupling members are retained in the unlocked position by the co-operating retainers. Upon first use, in order to assemble the appliance to the counterpart coupling element, the appliance is pressed against the counterpart coupling element. The press-fit coupling force being smaller than the first retention strength generally encourages a two-stage engagement effect. The counterpart coupling element is able to engage the coupling formation generally prior to the pressure causing relative displacement between the first and second members to the locked position. Once in the locked position, the bracing portion of the second member braces the coupling formation against deflection, thereby locking or securely attaching the appliance to the counterpart coupling element. In order to separate the appliance, the frangible portion is torn or broken, releasing the bracing effect. The first member may remain at least temporarily coupled to the counterpart coupling element, at least until an external force is applied to separate the two. However, the release of the bracing effect means that it becomes easier to separate the first member from the counterpart coupling element. Optionally, the second member may be moved away from the first member, exposing the first member and facilitating separation. The second member may be shaped or configured so as to at least partly shroud the first member at least when in the locked position.

The first and second aspects may be used independently of each other, or advantageously in combination.

A third aspect of the invention relates to an auxiliary device for a controlled discharge ostomy appliance. Whether or not the appliance includes a self-urging seal, and/or a coupling member initially held in an unlocked position, and/or a single-use feature, the fourth aspect provides a protector of molded plastics, the protector being configured to be releasably coupled to the appliance to form a combined assembly therewith, for protecting the body-facing portion of the appliance prior to use of the appliance.

The body-facing portion of the appliance typically includes at least a stoma seal for sealing engagement with a stoma in use, and a mounting device for mounting the appliance in an operative position at a stoma. The seal is, by its nature delicate and vulnerable to damage. Damage to the seal surface may reduce the efficacy of the stoma seal, and lead to premature leakage of stool during the normal wear-life of the appliance. The protector can also keep the surface of the seal clean, while enabling the appliance (with the protector assembled thereto) to be carried in a suitable bag, such as a hand-bag or brief-case, until fitted.

The protector optionally includes at least one of:
(i) a seal displacer manipulable by a user to displace a self-urging seal of the appliance to a non-deployed position prior to fitting the appliance at a stoma;
(ii) a substantially rigid coupling member guard portion for protecting a first member of the appliance from external forces that might otherwise push the first member from a unlocked position to a locked position;
(iii) a bracing portion for bracing and supporting a second member of the appliance, the second member including a frangible portion that is selectively breakable or tearable in use to release the appliance;
(iv) a fastener profile for cooperating with a periphery of the appliance, to couple the protector to the appliance to form a combined assembly therewith.

The protector may be configured to extend over and/or substantially cover a body-facing side of the appliance. The protector may have the form of a half-shell. The protector may include one or more concave or dished portions.

The seal displacer may be located at a centre of the protector.

The rigid guard portion may comprise a channel shaped fender, the fender extending in a closed loop to define an endless channel. The rigid guard portion may be reinforced, for example, by one or more ribs.

If the seal displacer and the rigid guard portion are both provided, the rigid guard portion may extend around the seal displacer. The rigid guard portion and the seal displacer may adjoin at, or be separated by, an interface profile that permits displacement of the seal displacer without substantial displacement of the rigid guard portion. The interface profile may, for example, comprise one or more folds, corrugations or pleats in the plastics material.

The bracing portion may comprise a step shaped recess in the protector, and extending around a closed loop shaped path.

The fastener profile may comprise one or more undercut lugs.

The protector may have a surface profile on one side that is generally the negative of the profile of the surface of the other. The protector may be made of plastics material that is sufficiently stiff to define a self-supporting shape, but is flexible to permit limited deformation (for example, for the seal displacer, and to permit the protector to be separated from the appliance). The protector may for example, be made of blow-molded, or vacuum-molded plastics.

In a related fourth aspect, the invention provides a plastics protector for a controlled discharge appliance, the protector comprising: an encircling rim portion disposed near or at the periphery of the protector; an annular step portion radially inwardly of the rim portion and extending towards a first side of the protector; an annular channel portion radially inwardly of the annular step portion, and extending further to said first side than the step portion; and a displaceable button portion disposed radially inwardly of the channel portion. The displaceable button portion may be less rigid than at least the channel portion. The channel portion may define a protection fender. The displaceable button portion may be joined to an inner wall of the channel portion via an interface region that permits manipulation of the button portion without substantial deformation of the channel portion. The displaceable button portion may be generally central, and the other portions arranged progressively outside the button portion.

In a related fifth aspect, the invention provides a controlled discharge ostomy appliance, the appliance comprising:

a first integrated module comprising: a top wall; a collapsible collector depending from the top wall at a first open end of the collector; and a first member of closed loop shape depending from the collapsible collector at a second open end of the collector; the first module defining a first chamber;

a second integrated module comprising: a second member including a bracing portion for cooperating with the coupling formation of the first member for bracing the coupling formation against outward deflection, the second member including a frangible portion for releasing the bracing effect when the frangible portion is broken; and a third integrated module comprising: a seal support wall and a seal membrane depending from the seal support wall, the seal support wall and the seal membrane defining a seal chamber in which is disposed a resiliently compressible component (e.g., a device or material); the third module being locatable in an operative position at least partly within in the first chamber of the first module with the seal support wall arranged close to the top wall.

The second member and/or module may generally have a closed loop form, and define a skirt profile around the first module. At least a portion of the top wall of the first module may be received in or at a respective aperture of the second member.

The second module is typically an integrally molded item consisting of the second member. The frangible portion may be defined by a line or region of relative weakness. In use, when a user tears or breaks the frangible portion, this may split the closed loop shape of the second member, breaking the loop into a discontinuous form.

The seal support wall may comprise or carry one or more ports for controlling fluid flow into and/or our of the seal chamber. At least one port may comprise a chimney that extends through an aperture in the top wall (when the modules are assembled together). Additionally or alternatively, at least one (other) port may communicate with a space between the seal support wall and the top wall (when the modules are assembled together).

The top wall (of the first module) and the seal support wall (of the third module) may together define a flatus vent space communicating with the first chamber around at least a portion of the periphery of the seal support wall. A deodorising filter and/or a phase separator may be disposed in the flatus vent space. When both are provided, the phase separator preferably shrouds the deodorising filter. The phase separator may, for example, comprise open cell foam, or some other material that allows passage of flatus while resisting passage of at least semi-solid (and optionally liquid) waste.

A coupling is provided for retaining the third module in the operative position with respect to the first module, optionally in conjunction with the second module. The coupling may comprise elements configured to form an interference (e.g. interlocking or tight friction) fit. The elements may include cooperating lugs on the seal support wall and the top wall, and/or inter-fitting surfaces of the chimney and the respective aperture of the top wall through which the chimney passes.

A coupling is additionally provided between the second module and at least one of the first and third modules, for retaining the modules in assembled condition. The coupling may comprises elements configured to form an interference (e.g. interlocking or tight friction) fit.

In a further aspect, a controlled discharge ostomy appliance assembly comprises (i) a stoma seal that is self-urging with a dynamic damping characteristic that resists changes of seal volume, (ii) a press-fit coupling member displaceable from an unlocked position to a locked position as part of a press-fit process, and (iii) a single-use frangible portion. The assembly further includes a protector shield removably coupled to the appliance forming a combined assembly therewith. The protector shield comprises (i) a seal displacer manipulable for displacing the stoma seal to a non-operative position ready for fitting, (ii) a substantially rigid protection portion for protecting the state of the coupling member, and (iii) a bracing portion for bracing the single-use frangible portion.

The above aspects may be used independently of each other of advantageously in combination. Various additional or alternative features, objects and advantages of the invention will be apparent to the skilled person from the following detailed description. Protection may be claimed for any novel feature or idea disclosed herein and/or in the drawings, whether or not emphasis has been placed thereon.

DETAILED DESCRIPTION OF PREFERRED EMBODIMENTS

The following description refers to all of the drawings, although certain drawings are selected to highlight the described features. The single preferred embodiment embodies multiple aspects of the invention, as described individually below. These aspects may be used independently of each other, or advantageously in combination as in the illustrated form.

Displacement of Seal Prior to Fitting Appliance at Stoma

A first aspect used in the preferred embodiment is provision for the seal to be displaced to make the appliance ready for fitting.

Figure 1:
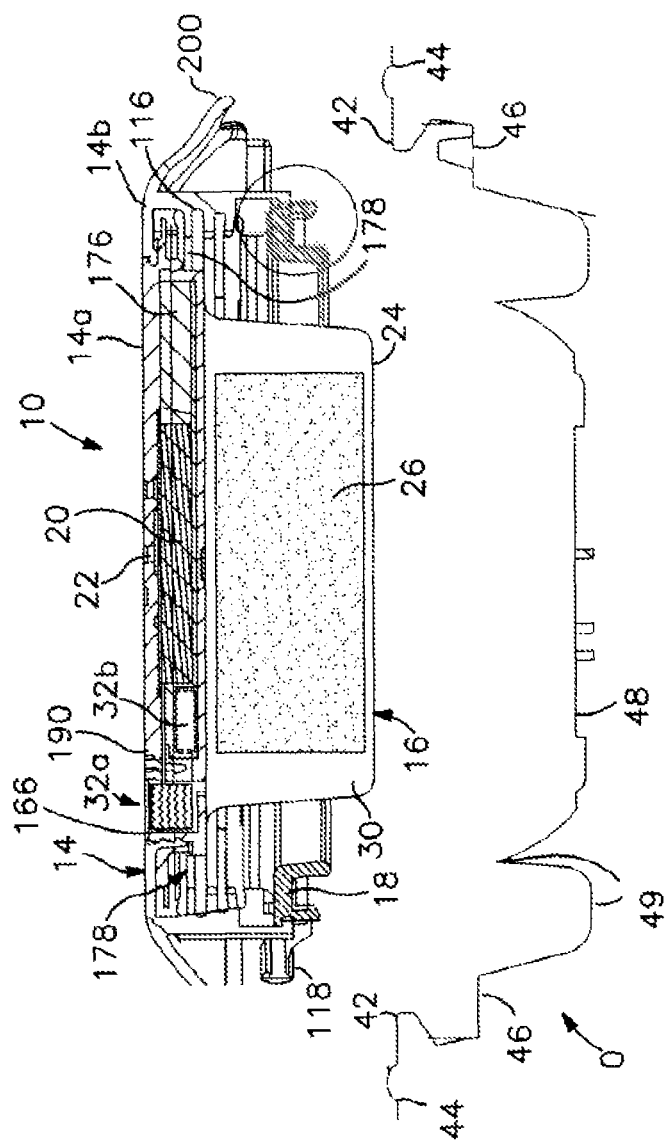
FIG. 1 is a schematic section through a preferred embodiment of controlled discharge ostomy appliance, with a shield protector in exploded view.
Figure 7:
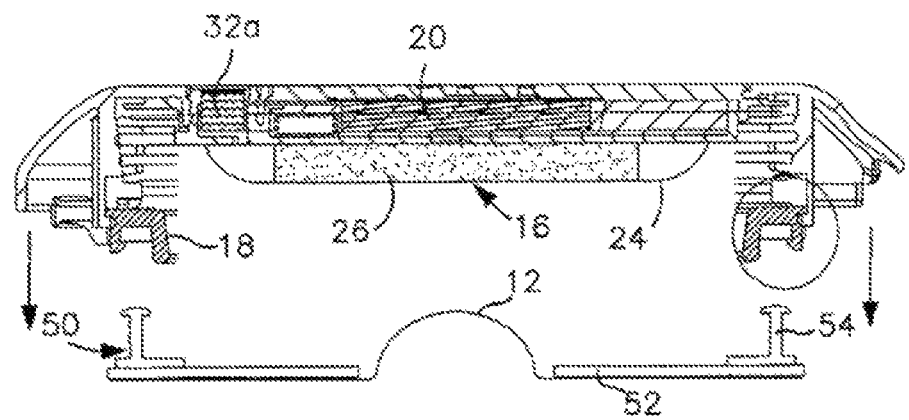
FIG. 7 is a schematic section showing fitting of the appliance at a stoma with the seal in the non-deployed state.
Figure 8:
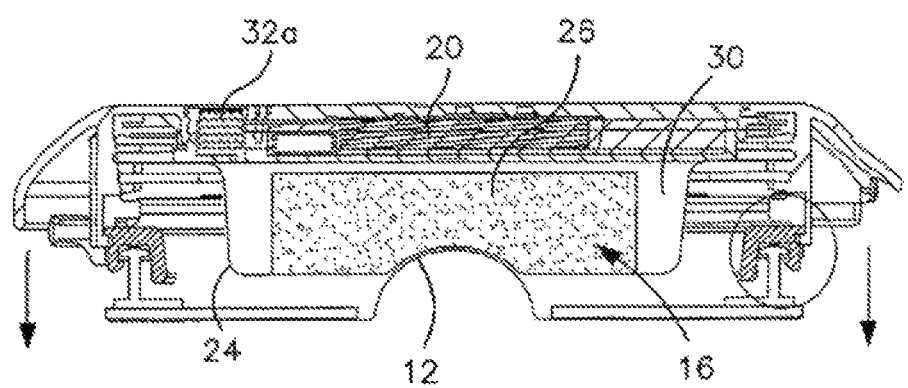
FIG. 8 is a schematic section showing the seal reaching a deployed state after initial fitting of the appliance.

Referring to the drawings, a controlled evacuation ostomy appliance 10 is illustrated for controlling discharge from a wearer's stoma 12 (FIGS. 7 and 8). The appliance 10 generally comprises a cover 14, a stoma seal 16, and a mounting device 18. While FIG. 1 shows these features as distinct items for ease of understanding, it will be appreciated that each feature may be made of several components, and that portions of plural features may be integrated together.

The stoma seal 16 is configured for sealing internally and/or externally against the stoma 12, in order to obstruct discharge of body waste. The seal 16 may be configured to obstruct discharge of at least solid waste, more preferably also semi-solid and/or liquid waste. The seal 16 may be configured to allow flatus gas to escape from the stoma 12, in order to avoid flatus accumulating uncomfortably within the stomal tract. Discharged flatus passes through a deodorising filter 20 and is vented to atmosphere via one or more outlet apertures 22 in the cover 14.

The seal 16 is of a self-urging type, which generates an urging force to apply a sealing force to the stoma. The term self-urging means that, once fitted and in use, the seal (or the appliance) generates its own urging force towards the stoma without reliance on application of a pressurization force from a source external to the appliance 10 (for example, using an external inflation pump, or applying a physical pumping force to the appliance). In the present embodiment, the seal 16 comprises a flexible membrane 24, and a resilient component 26 for urging the flexible membrane towards the stoma 12 in use. The resilient component 26 may take a variety of forms, such as a compressible fluid, and/or a member of resilient material. In the preferred form, the resilient component 26 comprises a member made of resiliently compressible plastics foam. The foam may be open cell foam. Suitable foam materials include polyurethane, cellulose, or olefin. Closed cell foams may also be desirable. An optimum three-dimensional form of the foam member is discussed later in relation to FIG. 16. The resilient component 26, when compressed, generates or maintains a return force on the membrane 24, thereby providing at least a component of the sealing pressure in use. The resilient component 26 may be supported by a support wall 28 of, or attached to, the cover 14.

The seal 16 further comprises a damping device that damps or resists certain motion or displacement of the membrane 24. The damping device may comprise a damping chamber 30 for damping fluid. The damping chamber 30 may accommodate the resilient component 26. The membrane 24 may form at least a portion of the wall of the damping chamber 30. A suitable damping fluid is, for example, air. The chamber 30 further comprises one or more ports 32a and 32b for controlling admission and/or discharge of the damping fluid into/from the damping chamber 30. For example, the port(s) 32a and 32b may restrict the rate of flow of damping fluid through the port (in a specific admission or discharge direction, or in both admission and discharge directions). Restricting the rate of flow of damping fluid slows the rate of changes in volume of the chamber 30, and hence damps motion of the membrane 24. Restricting admission of damping fluid through the port(s) 32 restricts the rate at which the seal 16 can expand to urge the membrane 24 against the stoma 12. Additionally or alternatively, restricting discharge of damping fluid through the port(s) 32a and 32b restricts the rate at which the seal 16 can shrink and/or move in a direction away from the body in use.

A variety of different configurations for the port(s) 32a and 32b are possible, to provide a variety of different possible damping characteristics. The damping characteristic may result from a compound effect of plural ports functioning in parallel with each other. In general, a desirable damping characteristic is one that comprises: (i) a restriction to admission of inflation fluid, to slow expansion or movement of the seal towards the stoma; (ii) a restriction to discharge of damping fluid, to slow compression or movement of the seal away from the stoma; and (iii) a pressure-relief effect to allow substantially unrestricted discharge of damping fluid should the pressure within the interior of the damping chamber 30 exceed the pressure outside the chamber by a predetermined threshold. The threshold may, for example, be at least 75 mmHg. The restriction to admission (i), and the restriction to discharge (ii), may be substantially equal to each other, or may be different in magnitude. In either case, both restrictions (i) and (ii) may be provided in common by a bidirectional port. Alternatively, the restriction to admission (i) and the restriction to discharge (ii) may be implemented by distinct unidirectional ports. The pressure-relief effect may be provided by an additional pressure-relief port, or it may be provided as an additional valve function of one of the other valves.

A highly practical configuration is a first port 32a that has a bidirectional characteristic that acts as a restriction to fluid flow in both the admission and discharge directions, to substantially the same degree. The first port 32a may be implemented by a piece of porous (e.g. microporous) material. The first port may define an airflow rate of between 0.1 cc/min and 15 cc/min under an applied pressure of between 5 mmHg and 40 mmHg. A second port 32b provides the pressure-relief function, the second port 32b comprising a valve that opens to create a substantially non-restricted path to discharge of fluid from the chamber 30 when the fluid pressure within the chamber 30 exceeds the external pressure by more than the aforementioned threshold.

At least one of the ports (here 32a) may communicate directly with the atmosphere outside the appliance. Additionally or alternatively, at least one of the ports (here 32b) may communicate directly with the space containing the flatus vent filter 20, such that the port communicates indirectly with external atmosphere via the filter 20.

The appliance 10 is initially fitted with a protector 40 that protects the body-side facing components of the appliance 10 prior to the appliance 10 being used. The protector 40 typically has the form of a shield, or another shape that follows the shape of the body-side face of the appliance. The protector 40 extends to cover substantially the entire body-side facing side of the appliance 10. The protector 40 may also encapsulate a peripheral edge of the appliance, in order to protect the appliance from side impacts. The protector 40 is releasably coupled to the appliance 10 by means of protector fastener lugs 42 that engage the periphery of the appliance 10 (e.g. the periphery of the cover 14) to form a combined assembly. Although the present embodiment illustrates a mechanical interfit by the protector fastener lugs 42, an adhesive fastener could be used alternatively or in addition.

The protector 40 comprises one or more sections selected from: a peripheral rim 44, an annular step 46, and a seal displacer 48. Optionally for this aspect, a substantially rigid mounting device guard portion (also referred to as a coupling member guard portion) 49 may also be provided for protecting the mounting device 18. Whether or not the rigid guard portion 49 is used, it may be seen that the protector fastener lugs 42 engage a portion of the appliance that is distinct from, and preferably also clear of, the mounting device 18. This can avoid stress on, or use of, the mounting device 18 prior to fitting the appliance at a stoma, so that the mounting device 18 is preserved in an optimum state for use.

The present embodiment comprises all sections, the annular step 46 extending radially inwardly of the rim 44, and the seal displacer being disposed radially inwardly of the step 46. The different sections are integrally formed as a one-piece plastics molding. The plastics molding may, for example, be vacuum molded or blow molded. The lugs 42 project inwardly from the rim 44, and define undercuts with respect to the annular step 46. The seal displacer 48 is generally centrally disposed, so that it is generally aligned with the seal 16 of the appliance 10. As well as protecting the seal 16, a significant function of the seal displacer 48 is to control or set the state of the seal 16.

In the present embodiment, the seal displacer 48 is molded to have an initial shape (FIGS. 1-4) that corresponds to, or at least accommodates or at least partly receives, the seal 16 when in a (near) fully distended state. The fully distended state is the state in which the seal membrane 24 is fully distended or expanded by the resilient device 26. The seal displacer 48 may accommodate the seal 16 in the fully distended state, or the seal displacer 48 may accommodate the seal 16 in a near fully distended state (e.g. a distended state that is similar to the fully distended state, even if the seal 16 is slightly compressed). The seal displacer 48 comprises a dished or cup section defining a pocket for cupping or receiving at least a portion of the seal 16.

Figure 5:
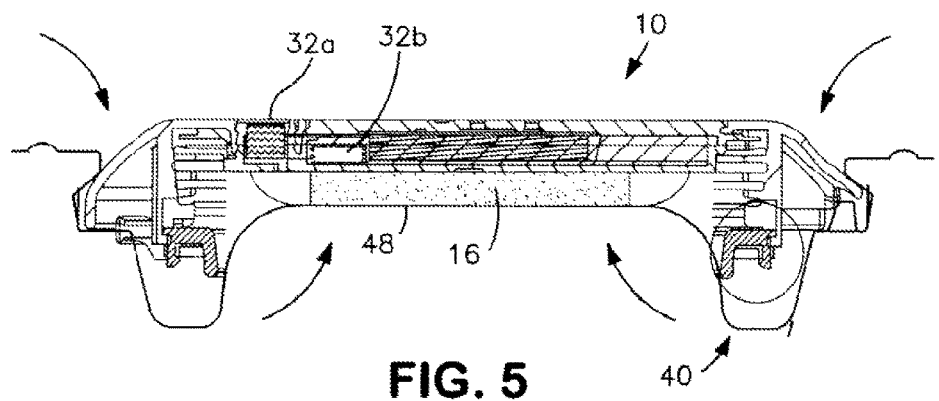
FIG. 5 is a schematic section illustrated displacement of the seal to a non-deployed position, using the protector shield, prior to fitting.

Referring to FIG. 5 at some time prior to fitting the appliance 10 at a stoma, the user (or other caregiver) presses the stoma displacer 48 to displace the seal 16 to a non-deployed state. Displacing of the seal causes the seal to compress or retract to a position and/or shape in which the seal 16 will not initially contact the stoma 12 when the appliance is fitted. Typically the user displaces the seal just prior to fitting the appliance 10, but the user could also displace the seal even earlier. As indicated in FIG. 5 by the arrows, the user may squeeze the appliance 10 with its protector 40 from above and below, for example, between opposed fingers and thumbs. The seal displacer 48 of the protector 40 deforms to displace the seal 16, while the protector 40 remains coupled to the appliance 10.

Although the port 32a tends to restrict discharge of fluid from the chamber 30, as soon as the pressure within the chamber exceeds the threshold, the second port 32b opens to allow fluid discharge from the chamber 30. As explained above, the threshold is relatively modest, and is easily exceed by manual application of finger pressure squeezing the seal. Therefore, provided that the user is reasonably dextrous and able to apply modest finger pressure to the seal displacer, the second port 32b will open to allow the seal 16 to be compressed readily without significant damping resistance. The seal displacer 48 may function to retain the seal 16 in its non-deployed state until the protector 40 is removed.

Figure 6:
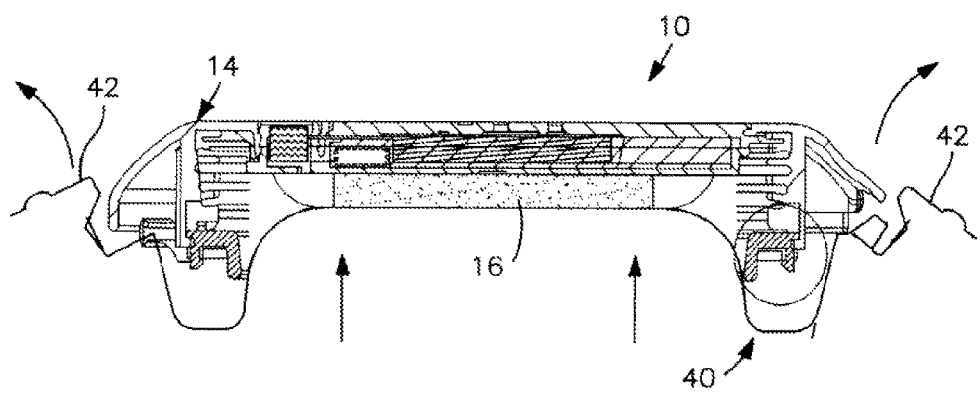
FIG. 6 is a schematic section showing separation of the shield protector from the appliance.

Referring to FIG. 6, the appliance 10 is separated or ejected from the protector 40. Typically, separation occurs once the seal 16 has been displaced. In the present embodiment, when pressure is applied between opposed fingers and thumbs, the seal 16 displaces progressively until it reaches its non-deployed state whereupon the pressure applied to the protector 40 then flexes the protector, releasing the fastening engagement between the lugs 42 and the cover 14 at least at one point around the periphery (and optionally all around the periphery). The separation of the appliance 10 from the protector is therefore a seamless part of the same operation as soon as the seal reaches its non-deployed state. In other embodiments, the protector 40 may be configured to remain fastened to the appliance 10 even once the seal 16 has been displaced to its non-deployed state, until some additional manipulation is made to release the engagement between the fastener lugs 42 and the cover 14.

Referring to FIG. 7, once the appliance 10 has been separated from the protector 40, the action of the seal displacer 48 on the seal 16 is removed, and the seal 16 tends to re-expand under the influence of the resilient device 26 inside the seal 16. The port 32a restricts the rate at which fluid can re-enter the chamber 30, thereby damping movement of the seal 16 and slowing the speed at which the seal membrane 24 can re-deploy towards its fully distended state. Preferably, once released from the non-deployed state, the seal 16 may expand relatively slowly over a period of a few minutes towards its fully deployed state, even though the resilient device 26 may itself tend to decompress over a matter of seconds were the damping effect to be removed. The port 32a may be configured such that the deployment time from non-deployed to fully deployed may be at least 1 minute, or at least 2 minutes, or at least 3 minutes, or at least 4 minutes, or at least 5 minutes, or at least 10 minutes.

The above arrangement gives the user sufficient time to fit the appliance 10 at the stoma 12 before the seal 16 advances significantly towards its deployed state. The appliance 10 is fitted in position using the mounting device 18. In the present embodiment, the appliance 10 is configured to be mounted to a body fitment 50 that is already worn on the body around the stoma 12. The body fitment 50 typically comprises an apertured pad of medical-grade skin-friendly adhesive 52, and a body-side coupling member 54 of closed loop shape surrounding the pad aperture. The mounting device 18 comprises an appliance-side (first) coupling member configured to form a mechanical (e.g. interference-fit or interlocking-fit) or adhesive coupling engagement with the coupling member 54. The coupling engagement may be releasable to enable the appliance 10 to be separated from the body fitment 50 after use, while the body fitment remains in situ on the body around the stoma 12. Alternatively (not shown), the mounting device 18 may be configured to mount the appliance 10 directly on the body instead of mounting to a body fitment 50 already worn on the body. In such case, the mounting device 18 may include a pad of adhesive equivalent to the adhesive 52 described above.

As depicted in FIG. 7, at the time of fitting, the seal membrane 24 is at or near its non-deployed position, out of contact with the stoma 12. The potential discomfort resulting from high contact pressure on the stoma 12 at fitting is therefore avoided. Also, the potential risk of a high reaction force weakening the adhesion between the body fitment 50 and the peristomal skin, is also avoided.

Referring to FIG. 8, once the appliance 10 is fitted at the stoma 12, the seal 16 continues to advance or expand progressively towards the stoma 12 under the urging force of the resilient device 26. At some time shortly after fitting (e.g. between 0.5 minutes and 10 minutes), the seal membrane 24 advances slowly into contact with the stoma 12, and conforms to the shape of the stoma 12. The initial contact pressure between the membrane 24 and the stoma 12 is less than would be applied by the resilient device 26 alone. This is because the damping effect of the port 32a resists the urging effect of the resilient device 26, thereby reducing the force applied to the membrane 24 by the resilient device 26. Once the seal 16 has fully conformed to the shape of the stoma 12, the chamber 30 reaches pressure equalization with external atmosphere, and the chamber volume 30 stabilizes. As the seal 16 approaches pressure and/or volume stabilization, the dynamic damping effect fades, and the contact pressure between the membrane 24 and the stoma 12 reaches that exerted by the resilient device 26. Deploying the seal 16 from a non-deployed condition enables the seal 16 more easily to conform to a natural shape of the stoma 12. Such a seal 16 can be extremely effective.

The contact pressure between the seal 16 and the stoma 12 comprises a static component and a dynamic component. The static component is generated by the resilience of the resilient device 26 that remains partly compressed by conforming to the stoma shape, and applies a resilient return force towards the stoma 12. The resilient device 26 is configured such that the passive component of the contact pressure does not exceed a predetermined limit value that might otherwise result in reduced blood perfusion in the stoma 12. For example, the predetermined limit value may be about 25 mmHg. The dynamic component of the contact pressure results from the port 32a regulating fluid flow to and from the chamber 30 of the seal 16, as the chamber volume adapts to follow any movement of the stoma 12. The port 32a defines a dynamic damping characteristic of adaptation of the seal, in addition to the effect of the resilient device 26. During expansion of the seal 16, the dynamic component is negative, reducing the contact pressure (as explained above during deployment of the seal); during compression of the seal 16, the dynamic component is positive, increasing the contact pressure. Such a self-urging design has the advantage that no external inflation source is needed, thereby avoiding the user having to carry such a separate device. The pressure inside the seal 16 is self-regulating, and the seal 16 can adapt to different volumes automatically. While the resilient device 26 permits a wide range of stoma shapes and sizes to be accommodated, the dynamic damping characteristic resists compression of the seal 16 should the stoma 12 begin to push outwardly. The fluid trapped in the chamber 30 by the damping characteristic generates a temporary, dynamic increase in the contact pressure exerted by the seal 16 to counter such a challenge from the stoma. A transient challenge may be caused by stool and flatus in the stoma, and the temporary increase in sealing pressure enhances the seal 16 against escape of stool, without the increased sealing pressure being exerted for too long to obstruct regular blood perfusion of the stoma. The damping characteristic only temporarily traps inflation fluid, thereby allowing the seal 16 to adapt in volume if the outward movement of the stoma 12 is more than transient. The pressure relief port 32b provides a further degree of security to ensure that the pressure in the chamber 30 does exceed the pressure relief threshold, even when the additional dynamic component is significant. The pressure relief port 32b opens to vent inflation fluid should the pressure relief threshold be exceeded.

The technique of displacing the seal 16 to a non-deployed position prior to fitting the appliance, enables the dynamic damping effect to be used advantageously both during fitting, as well as in use, of the appliance 10.

Displaceable Appliance Coupling Member

A second aspect of the preferred embodiment relates to a coupling member arrangement for making a press-fit with a body-side coupling member for fitting the appliance at a stoma. This aspect may be used in combination with the first aspect, or independently of the first aspect. The following description focuses on a coupling for the appliance, but this embodiment may also use any combination of features from the first embodiment as if described in whole combination.

Figure 9:
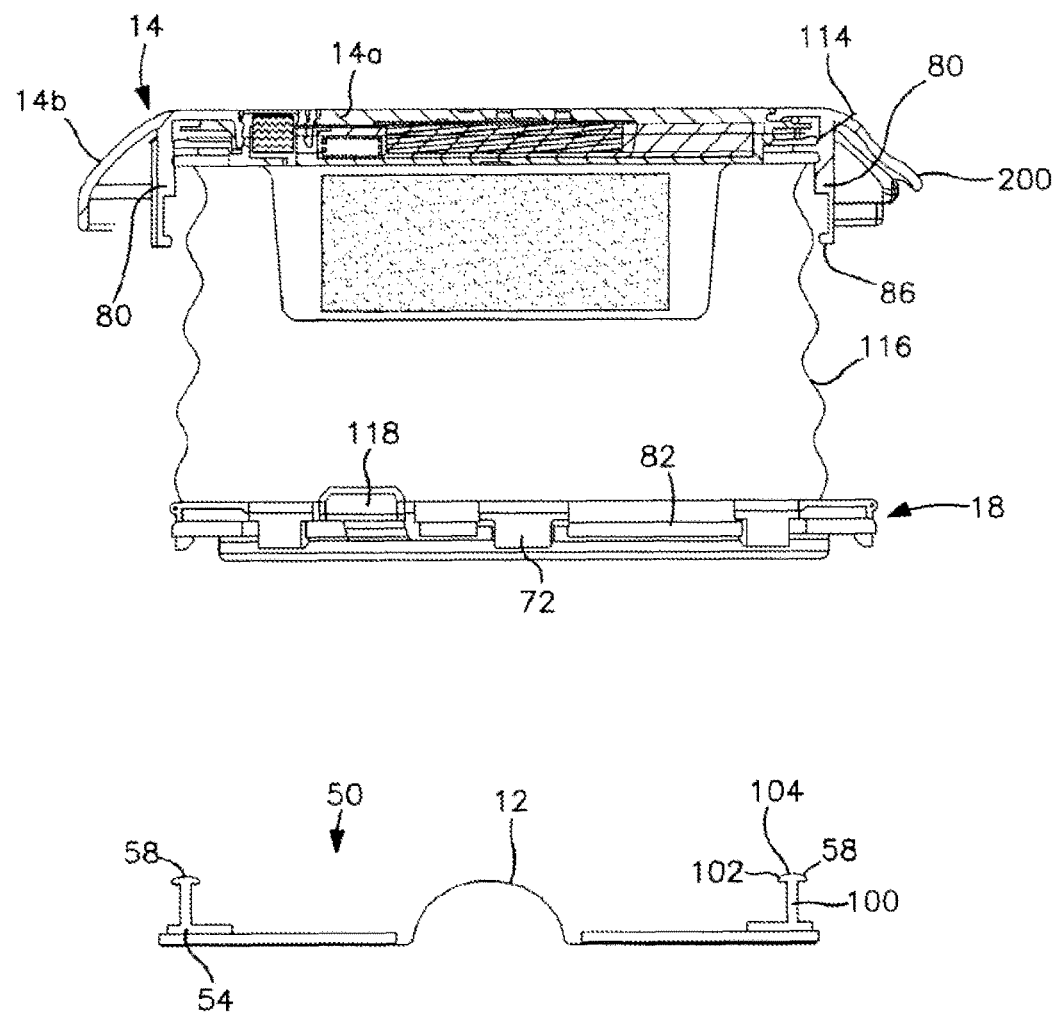
FIG. 9 is a schematic section and exploded view of the appliance, illustrating a relation between an appliance coupling member, and a body-side fitment.
Figure 10:
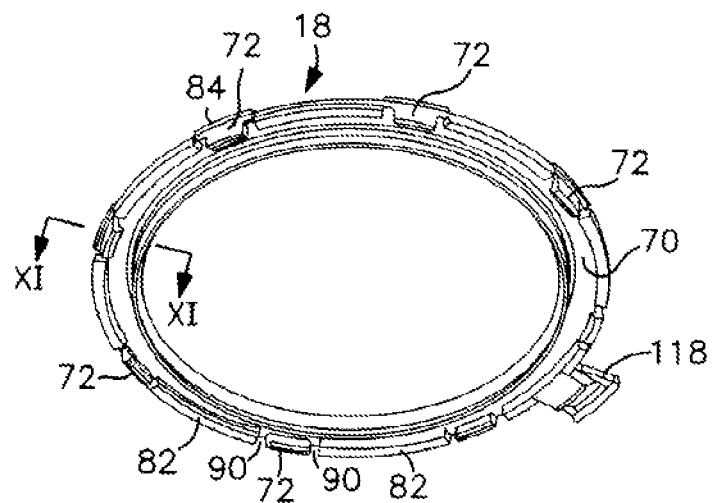
FIG. 10 is a schematic underside perspective view of the appliance coupling member in isolation.
Figure 11:
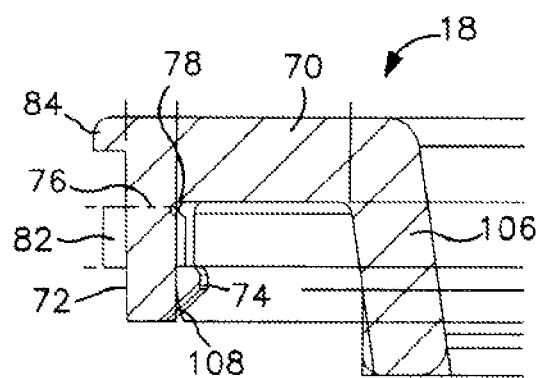
FIG. 11 is a schematic section along the line XI-XI of FIG. 10, on an enlarged scale.

As best seen in FIGS. 9-11, the mounting device comprises a first member (first coupling member or appliance-side coupling member) 18 distinct from the cover 14 (second member). The first member 18 is of closed loop shape (e.g. annular in this embodiment). The first member 18 has a base 70 carrying a coupling formation for mechanically engaging the body-side coupling member 54 of the body fitment 50. The coupling formation comprises a plurality of lugs 72 depending from the base 70 at spaced apart positions around the periphery of the base 70. Each lug 72 has a radially inwardly projecting, undercut tooth 74 near its tip. The tooth 74 is configured for mechanically engaging a bead 58 of the body-side coupling member 54. Each lug 72 is able to flex, or deflect from its normal position, with respect to the base 70, independently of other lugs 72 to permit engagement and disengagement of the body-side coupling member 54. Each lug 72 may include a hinge or pivot portion 76 (FIG. 8) about which flexing of the lug 72 is promoted. The hinge or pivot portion 76 may optionally be defined by a thinned portion 78 (or some other material weakening) of the lug 72, or at the junction between the lug 72 and the base 70.

Figure 12:
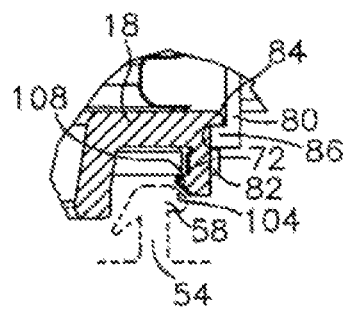
FIG. 12 is a schematic section showing on an enlarged scale a detail from an encircled portion of FIG. 1, and showing approach of the appliance coupling member to a body-side coupling member (shown in phantom).
Figure 13:
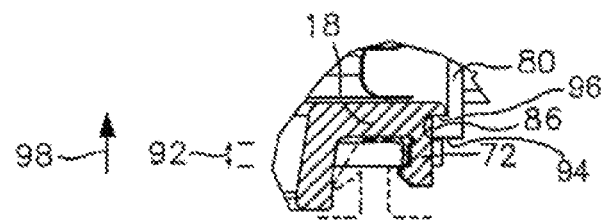
FIG. 13 is a schematic section similar to FIG. 12, but showing a first stage of engagement with the body-side coupling member (shown in phantom), with the appliance coupling member in the unlocked position.
Figure 14:
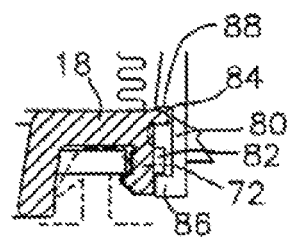
FIG. 14 is a schematic section similar to FIG. 12, but showing a second stage of engagement with the body-side coupling member (shown in phantom), with the appliance coupling member displaced to the locked position.
Figure 15:
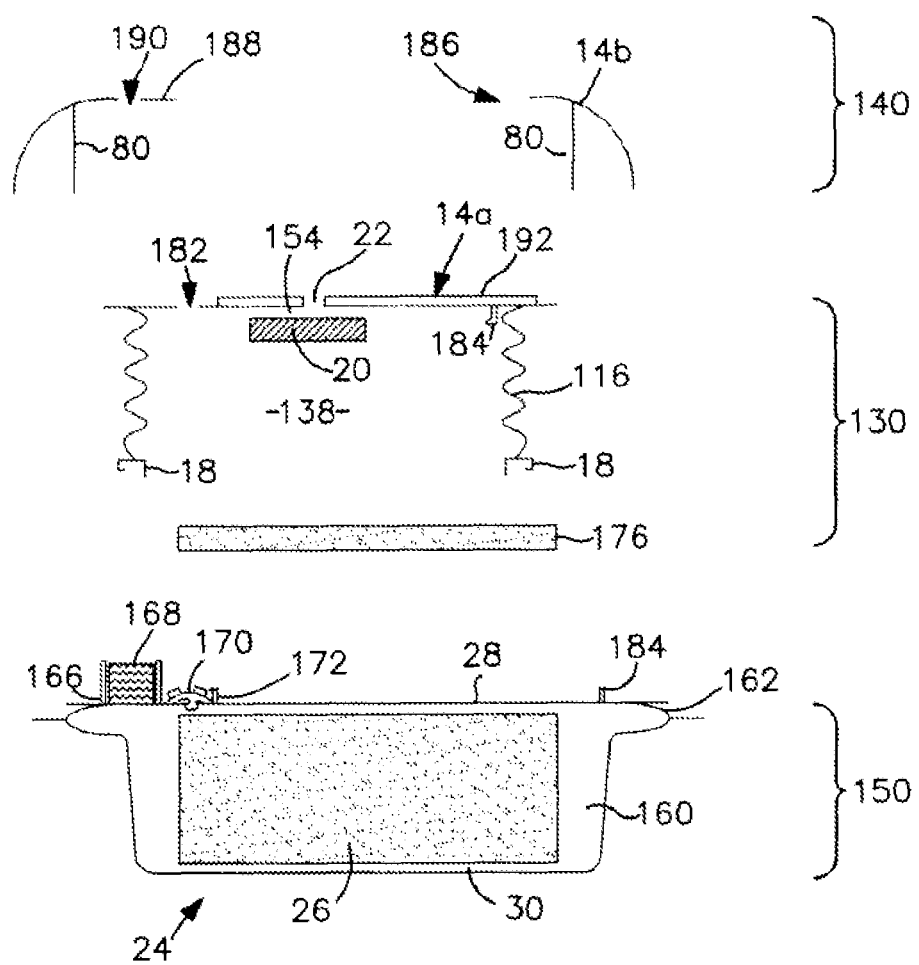
FIG. 15 is a schematic section showing, in exploded view, a modular construction of the appliance.

The cover 14 may comprise a top wall 14a, and a skirt 14b around the top wall 14a. The top wall 14a and the skirt may be integral, or they may be distinct parts assembled together. The first member 18 is movably supported by a bracing portion 80 of the cover 14. The bracing portion 80 is of closed loop shape and depends from, e.g., the skirt 14b of the cover 14. In FIG. 9, the first (appliance coupling) member 18 is shown separated from (or floating with respect to) the cover 14 and bracing portion 80, but FIGS. 12 and 13 show the first member 18 in a first unlocked position with respect to the bracing portion 80, and FIG. 14 shows the first member 18 in a second locked position with respect to the bracing portion 80. The degree of axial overlap between the bracing portion 80 and the first member 18 controls the degree to which the lugs 72 are free to flex to permit engagement or disengagement of the body-side coupling member 54 with respect to the first member 18. In the first unlocked position, the lugs 72 are not substantially blocked by the bracing portion 80, and the lugs are relatively free to flex outwardly. In the second locked position, the lugs 72 are substantially blocked or braced by the bracing portion 80, effectively locking the lugs 72 against flexing outwardly.

The first member 18 is retained captive relative to the bracing portion 80 by co-operating retainers (e.g. 82-88 in the present embodiment) provided at least one on the first member 18 and at least one on the bracing portion 80 (or other portion of the cover 14). Functions of the retainers may include one or more of:

(i) retaining the first member 18 and the bracing portion 80 of the cover 14 (second member) initially in the unlocked position with a first retention strength until pressure is applied to cause relative displacement to the locked position; and (ii) retaining the first member 18 and the bracing portion 80 of the cover 14 (second member) in the locked position with a second retention strength.

The second retention strength may optionally be greater than the first retention strength. One or both retention strengths may depend on whether or not the first member 18 is engaged with the body-side coupling member 54, as such engagement may restrict flexibility or deformability of the first member 18.

Various arrangements of retainers are envisaged. Purely by way of example, in the present embodiment, the retainers include one or more of:

(a) first retainers 82 in the form of bead segments depending from the base 70 and interspaced between the lugs 72. The first retainers 82 project radially outwardly beyond the base with an overlapping staircase-like profile. The lugs 72 and first retainers 82 alternate in a peripheral direction, around the periphery of the first member 18. Gaps 90 may be provided between the confronting edges of the first retainers 82 and the lugs 72.

(b) second retainers 84 in the form of flange-like or fin-like segments projecting from the base 70, at a level spaced from the first retainers 82 by an axial separation 92. The second retainers 84 are aligned with the pitch positions of the lugs 72, but project radially outwardly of the base 70, for example. The second retainers 84 each have a length that is generally equal to the spacing between consecutive first retainers 82, which facilitates molding. Alternatively, the second retainers 82 could be of other length(s), or merged together into a single second retainer (not shown) extending as a substantially continuous fin or flange around the entire periphery of the base 72, although this might require a more complex molding tool.

(c) third retainers 86 at the tip of the bracing portion, and defining inwardly directed teeth or castellations. The third retainers 86 have pitch positions corresponding to the pitch positions of the lugs 72, such that the third retainers 86 may overlap the second retainers 84 corresponding to each lug 72. Each third retainer 86 may also have an angular length in the peripheral (e.g. circumferential) direction that is longer than the spacing of consecutive first retainers 82, such that each third retainer may also overlap the ends of the two first retainers 82 on either side of a respective lug 72.

(d) a fourth retainer 88 in the form of a radially inwardly directed annular shoulder of the bracing portion 80.

The cooperation between the retainers 82-88 is as follows:

When the first member 18 is in the first unlocked position (FIGS. 12 and 13), the first and second retainers 82 and 84 generally overlap with, and engage opposite faces of, the third retainer 86. The third retainer has an axial thickness that is not greater than the spacing 92. The first retainers 82 engage or confront a body-facing side 94 of the third retainer 86, and the second retainers 84 engage or confront an opposite non-body-facing side 96. This engagement supports and retains the first member 18 in the first unlocked position with the first retainer strength, until a force is applied in a first direction 98 exceeding the first retainer strength, to displace the first member 18 relative to the bracing portion 80 towards the second locked position.

When the first member 18 is displaced to the locked position (FIG. 14), the fourth retainer 88 functions as a stop that engages the first retainer 82 to limit the extent of the displacement. The second retainer 84 snaps over and engages behind the third retainer 86. In effect, the second retainer 84 moves from engaging the body-facing side 94, to the non-body-facing side 96 of the third retainer 86. The new engagement between the second and third retainers 84 and 86 retains the first member 18 in the second locked position with the second retainer strength. The relative magnitudes of the first and second coupling strengths may be determined by the shapes of the first and third retainers 82 and 86, respectively. For example, the faces that engage when in the first unlocked position may have a smaller overlap and/or a larger degree of ramping or rounding, compared to the faces that engage when in the second locked position. Such shaping may define the first retention strength to be smaller than the second retention strength.

Having described the engagement between the first member 18 and the bracing portion 80 of the cover 14, the engagement between the first member 18 and the body-side coupling member 54 is now described. Many different designs of interengaging profiles for the first coupling member 18 and the body-side coupling member 54 may be used that provide a press fit (press-together) engagement and/or disengagement when the first member 18 is not substantially braced by the bracing portion 80 (first unlocked position), and a secure locked-together engagement when the first member 18 is substantially braced by the bracing portion 80 (second locked position). In the presently preferred embodiment, the body-side coupling member 54 generally comprises an upstanding cylindrical wall 100 having at its distal end the annular bead 58 projecting radially outwardly, and a seal portion 102 directed generally inwardly. The leading edge of the annular bead 58 includes a rounded or ramped lead-in surface 104.

The first member 18 consists of an annular channel that is open towards the body-side coupling member 54. The channel includes the base 70, a generally continuous inner wall 106 depending from the base 70, and a generally discontinuous outer wall defined by the combination of the lugs 72 and the first retainers 82 around the periphery of the base 70. The leading edge of each lug 72 also includes a rounded or ramped lead-in surface 108. The inner wall 106 defines a seal seat for engaging the seal portion 102 of the body-side coupling member 54 in the assembled condition.

In use (FIG. 9), the body fitment 50 is adhered to peristomal skin at the stoma 12 prior to fitting the appliance 10. The use of a separate body fitment 50 allows a succession of different appliances 10, and optionally one or more ostomy pouches (not shown) to be worn involving far fewer changes of body fitment 50, and therefore less distress for the peristomal skin. With the appliance 10 initially in its first unlocked position (FIG. 12), the appliance 10 is prepared for fitting by being held by hand so that the first member 18 faces, and is generally aligned with, the body-side coupling member 54. From that position, the appliance 10 is fitted by simply pressing the appliance by hand on to the body fitment 50.

Referring to FIGS. 12 and 13, pressing the appliance 10 causes the tip of the cylindrical wall 100 to enter the channel profile of the first member 18. Initially, the lead-in surfaces 104 and 108 of the bead 58 and the lugs 72 contact each other, and some of this contact force will also be applied onwards to the retainers 82 and 86 supporting the first member 18 in its unlocked position. However, in the unlocked position, the lugs 72 are not substantially braced, and have a weaker resistance than the first retention strength. The result is that the lugs 72 may deflect or flex outwardly under relatively low contact force before there is much tendency for the first member 18 to move out of the unlocked position. The lead-in surfaces 104 and 108 bearing on each other therefore cause the lugs 72 to flex, allowing the bead 58 to pass over and engage behind the tooth 74 of each lug 72 (FIG. 13). The lead in surfaces 104 and 18, and/or the lack of significant resistance of the lugs 72, contribute significantly to a low press-fit assembly force.

Once this initial stage of engagement has been reached, the retainers 82 and 86 become subjected to the full force of the appliance 10 being pressed on to the body fitment 50. The full force exceeds the first retention strength, causing the first coupling member 18 to displace into the cover 14, from the first unlocked position to the second locked position (FIG. 14). In the locked position, the bracing portion 80 substantially prevents outward flexing or deflection of the lugs 72, thereby locking the engagement between the first member 18 and the body-side coupling member 54. The body-side coupling member 54 is therefore trapped in engagement with respect to the first member 18, and the appliance securely fastened to the body fitment 50.

It will be appreciated that the above two-stage coupling action using the first member 18 and the bracing portion 80 of this embodiment achieves several significant advantages:
(i) The appliance is attached using a straightforward press-fit action, not requiring manipulation of any separate or additional locking device. Full locking engagement is achieved upon simple press-fitting. Although there are two separate stages of engagement, the user is unaware because one stage follows immediately from the previous stage under the same press-fit force.

(ii) The appliance is attachable using merely a relatively low assembly force for press-fitting the appliance to the body fitment, while the first member is in the unlocked position. The low assembly force does not compromise the final security of the attachment.

(iii) The final security of attachment is defined at least partly by the effect of the bracing portion that braces the first member when the first member is displaced to the locked position. This enables a significantly greater coupling strength than would be achieved using a conventional press-fit coupling assemblable by similar assembly force. In particular, the coupling strength is eminently suited for withstanding the seal support and/or reaction forces encountered in a controlled discharge ostomy appliance including a seal pressing on the stoma. This may include the additional dynamic seal force that may result from the damping effect described in the first embodiment.

At least one (or each) third retainer 86 may optionally be shaped to include a guard portion (not shown) at a position corresponding to a respective lug 72. The guard portion projects radially inwardly to a greater degree than the remainder of the third retainer 86. The guard portion is dimensioned to more tightly brace the lug 72 than the remainder of the third retainer 86, thereby enhancing or guarding the bracing effect. The guard portion is dimensioned so that it does not extend to overlap with the first retainers 82, and so it does not interfere with displacement of the first member 18 from the first unlocked position to the second locked position.

It will be appreciated from the foregoing description that the correct two-stage engagement may depend on the first member 18 being in its correct (first) unlocked position prior to fitting of the appliance 10 to the body fitment 50. In one form, the first member 18 is made of plastics of a significantly and/or strikingly different color from the cover 14 so that the relative position of the first member 18 can easily be ascertained from a visual inspection. For example, the cover 14 may be of a skin-like color, such as a light brown or fawn, or the cover 14 may be of a neutral color such as translucent. The first member 18 may be colored to have a contrasting color such as a primary color (e.g. blue or red). In the initial unlocked position (any of FIGS. 2, 5-7, 12, 13), which is the correct position prior to fitting, the first member 18 should project significantly beyond the bracing portion 80, and so the contrasting color of the projecting first member 18 should be easily visible from a side view of the appliance. If the contrasting color is not visible, this may indicate that the first member 18 may have accidentally been displaced to the locked position. Either the user should attempt to correct the position of the first member 18 (if the design of the appliance permits this), or the user should dispose of the appliance (or return it for refurbishment) as being not suitable for use.

Similarly, after fitting, the first member 18 should be correctly in its locked position (FIGS. 8 and 14). In the locked position, the first member 18 is substantially shrouded by the bracing portion 80 of the cover 14. By viewing the appliance 10 after fitting (e.g. looking downwardly at a side view of the appliance, possibly with the aid of a mirror to see other sides of the appliance), the contrasting color of the first member 18 should not be substantially visible. If the contrasting color is visible, this may indicate that the first member 18 has not been displaced fully to its locked position, meaning that the appliance might not be securely attached. The user can either try to re-apply pressure to press the appliance 10 progressively at different peripheral positions to correct the attachment, or the user may remove the appliance 10 knowing that the fitting was not correct.

The above use of contrasting color for the first member 18 can therefore provide important indications of the state of the appliance, allowing a user to visually ascertain the state quickly, easily and intuitively. In the vast majority of cases, no remedial action will be needed, and the identification of the operation state is merely to confirm to the user that the appliance 10 is functioning correctly. The identification of the operation state may also aid in the training of an ostomate to correctly use the appliance 10.

Referring to FIGS. 1-4, a further optional feature of the preferred embodiment is the provision of a protector 40 initially fitted to the appliance 10 to protect the body-side facing components of the appliance 10 prior to the appliance 10 being used. As in the first embodiment, the protector 40 typically has the form of a shield. The protector 40 extends to cover substantially the entire body-side facing side of the appliance 10. The protector 40 is releasably coupled to the appliance 10 by means of fastener lugs 42 that engage the periphery of the cover 14, to form an integral assembly.

The protector 40 comprises one or more sections selected from: a peripheral rim 44, an annular step 46, and a coupling member guard portion 49. The present embodiment comprises all three sections, the annular step extending radially inwardly of the rim 44, and the guard portion 49 being disposed radially inwardly of the step 46. The different sections are integrally formed as a one-piece plastics molding. The lugs 42 project inwardly from the rim 44, and define undercuts with respect to the annular step 46. The guard portion 49 serves to protect the first member 18. The guard portion 49 is spaced from the first member 18 to isolate the first member from impacts or other external forces received from the body-facing side, that might otherwise risk displacing the first member 18 to is locked position. The protection portion 49 is of a material thickness and/or shape to give it a generally rigid or stiff, self supporting form. For example, the guard portion 49 may include ribs 49a or other reinforcement shape. The guard portion 49 may have the form of a channel-shaped fender, and extend in a closed loop to define a closed loop channel. The protector 40 is separated from the appliance 10 prior to fitting the appliance.

The invention envisages various possible designs for releasing or relaxing the attachment to the body-side coupling member 54 when the user desires to remove the appliance 10 after it has been used. In one form (not shown), the cover 14 may be shiftable from the locked position back to the unlocked position, in order to remove the bracing effect on the lugs 72, and allow easier separation. However, in the second embodiment, the appliance 10 includes the following additional features:

(i) a single-use feature of the cover 14 for obstructing attachment of the device to the body fitment 50 more than once. The single-use feature optionally comprises at least one frangible portion 114 of the cover. The frangible portion 114 may extend into or through the bracing portion 80. The single use-feature 114 is optionally associated with a grippable tab 200

(ii) an expandable/collapsible waste collector 116 having an entrance opening sealed to the first member 18, to define an entry for stomal waste once the sealing effect is removed. The waste collector 116 is also sealed to the cover 14, for example at an opposite end. The portion sealed to the cover 14 may be closed, or it may be open to facilitate venting of flatus through the cover. The waste collector 116 is typically made of flexible plastics film. The waste collector 116 may be generally tubular, although many other shapes are possible.

In an initial state of the appliance 10 ready for fitting at a stoma 12, the waste collector 116 is folded to a collapsed state (FIGS. 1-4 and 12) in which the waste collector 116 is accommodated within the cover 14. The waste collector 116 permits displacement of the first member 18 from the unlocked to locked positions, as required for proper fitting of the appliance.

Figure 17:
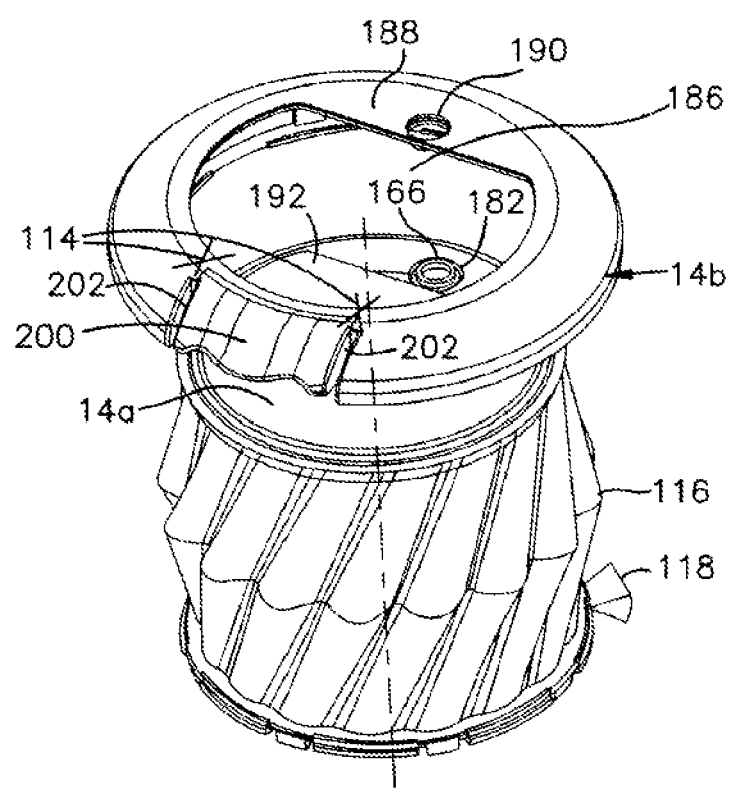
FIG. 17 is a schematic perspective view showing the second and third modules of the appliance.

In use, when the user desires to remove the appliance 10, the user manipulates the cover 14 to tear the frangible portion 114. The user may do this using the tab 200. This relaxes or removes the bracing effect of the bracing portion 80 around the first member 18, allowing the cover 14 to float relative to first member 18 (FIGS. 9 and 17). Floating the cover 14 away from the first member 18 removes the stoma seal 16 from the stoma 12, and distends or deploys the waste collector 116. With the effect of the stoma seal 16 removed, some stomal discharge may occur, but such discharge is contained by the waste collector 116. The first member 18 remains attached to the body-side coupling member 54 to define a contained volume for the stoma discharge, and avoid soiling. Although the strength of attachment between the first member 18 and the body-side coupling member 54 is reduced by removal of the bracing portion 80, the removal of the stoma seal 16 also removes any substantial reaction forces needing to be applied from the appliance 10 through the body fitment 50. Therefore, the relatively weak attachment of the first member 18 to the body-side coupling member 54 is eminently adequate while stomal discharge takes place into the waste collector 116. Once stomal discharge has stopped, the user may easily separate the first member 18 from the body-side coupling member 54 to totally separate the used appliance 10 for disposal. A handle 118 may be provided on the first member 18 to facilitate peeling the first member 18 from the body-side coupling member. The handle 118 may be implemented as an integrally formed tab or extension of the first member 18. In normal use of the appliance (e.g. in the first unlocked, and/or second locked position, see FIGS. 1, 2, 7 and 8), the handle 118 is shrouded by the cover 14, and only becomes accessible once the cover 14 has been floated from the first member 18. The bracing portion 80 of the cover 14 may include a recess or clearance for accommodating the projecting handle 118.

The single-use feature preferably prevents any attempt to reuse the appliance 10. Depending on the design of the appliance 10, the seal 16 in particular may be intended to be used reliably only a single time, and it may be difficult to clean a used appliance 10 to the proper degree of hygiene and sterility. The waste collector may also be difficult to collapse to a tightly folded condition that does not impinge on the seal face.

Protector for Accommodating Both Seal Displacement and Movable Coupling Member

The preferred embodiment combines both the aspect of seal displacement, and the aspect of a movable coupling member. The combination places additional design constraints on the protector 40. Referring to FIG. 1, it will be appreciated that the seal displacer 48 neighbors the coupling member guard portion 49 for protecting the coupling member 18. The two portions 48 and 49 of the protector have opposed design constraints. The seal displacer 48 is intended to be manipulated and displaced by a user without too much effort. In contrast, the guard portion 49 is intended not to be deformed, as any deformation might risk pressure being applied accidentally to the coupling member 18 that could displace the coupling member 18 to its incorrect locked position.

Figure 2:
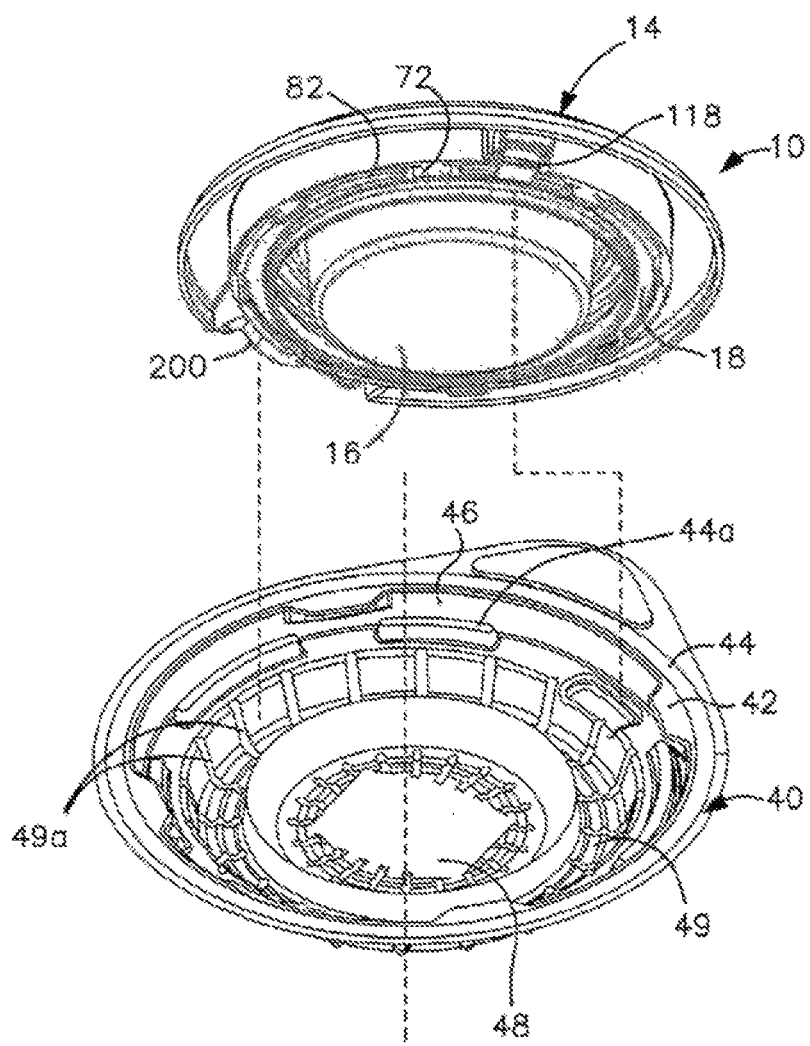
FIG. 2 is a schematic exploded perspective view of the components of FIG. 1.

As best seen in FIG. 2, the guard portion 49 is configured to be substantially rigid. The rigidity is aided by plural reinforcing ribs 49a. Each rib 49a extends in a generally radial direction to resist collapse of the guard portion 49.

The guard portion 49 and the seal displacer 48 adjoin one another at an interface portion. The interface portion includes a movable or bendable portion (such as one or more folds, or corrugations) that permits displacement of the seal displacer 48 without interfering with the guard portion 49. The seal displacer 48 of the interface portion may optionally include an overcentered portion that tends to flip between a first limit position (corresponding to the fully deployed state of the seal 16), and a second limit position (corresponding to the non-deployed position of the seal 16).

Figure 3:
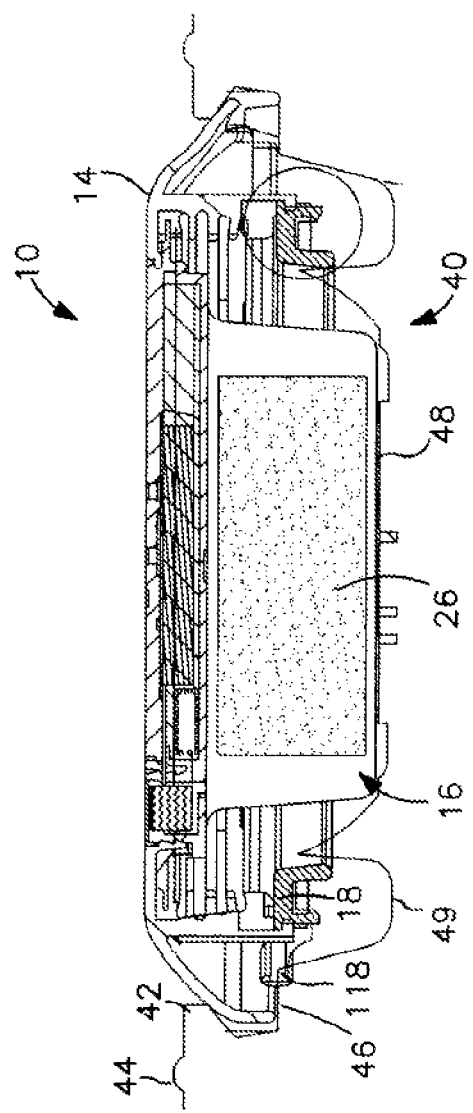
FIG. 3 is a schematic section similar to FIG. 1, showing the protector shield fitted to the appliance as a combined assembly prior to fitting.
Figure 4:
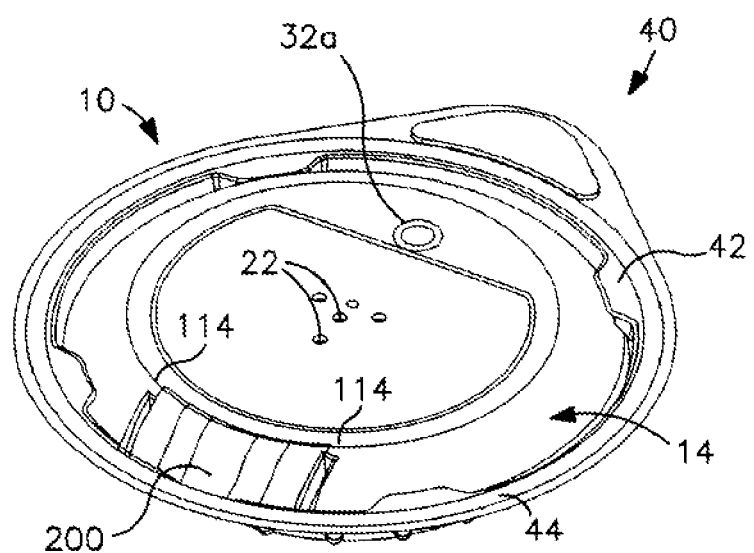
FIG. 4 is a perspective view from above of the components of FIG. 3.

In addition, the protector 40 serves to brace the single-use frangible portion 114 of the skirt 14b, to prevent any accidental tearing of the frangible portion 114, or lifting of the tab 200, prior to first use. As can be seen in FIGS. 3 and 4, the rim 44, in combination with the retainer lugs 42 brace the skirt 14b. As may also be seen in FIG. 2, additional upstand lugs 44a in the floor of the annular step 46, also serve to anchor the skirt 14b and the bracing portion 80 in a predetermined, supported position with respect to the protector 40, such that the skirt 14b is comprehensively protected by the protector 40.

Modular Construction of Appliance

A further aspect of the preferred embodiment focuses on a modular construction of the appliance 10. Referring to FIGS. 1 and 15-17, the appliance 10 generally comprises one or more of:

(i) A first integrated module 130 comprising: the top wall 14a of the cover; the collapsible waste collector 116; and the first member 18. The waste collector 116 depends from the top wall 14a, and the first member 18 depends from the waste collector 116. The waste collector 116 includes a first open end sealed to the top wall 14a, for example near the periphery of the top wall 14a. The waste collector 116 includes a second open end, corresponding to the waste entrance of the collector 116, that is sealed to the first member 18. The first member 18 thus provides the mouth of the waste collector 116, and the top wall 14a closes the opposite end. A chamber 138 is defined within the waste collector 116.

(ii) A second integrated module 140 comprising the skirt 14b (second member) of the cover 14. The skirt 14b is of closed loop shape, and comprises the bracing portion 80 for cooperating with the lugs (coupling formation) 72 of the first member 18 for bracing the lugs against outward deflection. The skirt 14b includes the frangible portion 114 for releasing the bracing effect when the frangible portion 114 is broken. The frangible portion 114 extends through the bracing portion 80.

(iii) A third integrated module 150 comprising: the seal support wall 28; and the seal membrane 24. The seal membrane 24 depends from the seal support wall 28. The seal support wall 28 and the seal membrane 24 together defining the seal chamber 30 in which is disposed the resiliently compressible device 26.

The modules 130, 140 and 150 are assemblable together to form a combined assembly of the appliance 10.

Preferred details of the modules include:

The first module 130 further comprises the deodorising filter 20 communicating with outlet apertures 22 in the top wall 14a. Various different techniques for mounting the filter 20 are possible. The preferred technique is to mount the filter 20, e.g. by welding, to a carrier film of material that is substantially impermeable to flatus gas. The carrier film is itself mounted to the top wall 14a, e.g. by welding, at a position outside the periphery of the filter 20. Such a construction has two advantages. Firstly, it enables a preferred technique of welding to be used, whereas the thickness of the materials might make welding impossible to use to join the filter 20 directly to the top wall 14a. Secondly, the carrier film defines an outlet plenum 154 between the top wall 14a and the filter 20, allowing for improved distribution of flatus to outlets 22 that are slightly spaced apart from each other, and some are not in register with the filter exit. The filter 20 is of a lateral flow type. Flatus enters the filter at its periphery (arrows) and flows laterally (e.g. radially inwardly) in the filter material to exit the filter near its centre (arrows). The carrier film includes one or more apertures that communicate with the exit of the filter 20 to allow deodorised flatus to enter the outlet plenum 154.

In the third module 150, the resilient device 26 typically comprises a piece of resilient foam material, for example, Polyether Polyurethane Open-Cell foam. The foam may have an Indention Force Deflection in the range of 20-40 lb suitable for generating the static component of the stoma sealing force when the foam is compressed against the stoma in use. At least one face 164 of the foam may have a non-smooth surface pattern, such as dimpled or with undulations, projections or channels (typically defining surface variations of less than 5 mm in height). The non-smooth surface provides small local variation in force applied through the membrane 24 to the stoma 12 in use, to promote separation and evacuation of flatus at the interface between the seal membrane 24 and the surface of the stoma 12. In the present embodiment, both faces of the foam member 26 have non-smooth surfaces, in order to allow the foam to be fitted either way up, thereby simplifying assembly.

The seal membrane 24 comprises two membrane portions 160 and 162. The first membrane portion 160 is of inverted-top-hat shape, for example, comprising an annular flange 160a from which depends a well 160b having a seal face 160c. The seal face 160c may be smooth, or it may have a substantially non-smooth surface, for example, with fine undulations, projections or channels (typically defining surface variations of less than 1 mm in height, preferably less than 0.5 mm). The non-smooth surface promotes separation and evacuation of flatus at the interface with the stoma while obstructing passage of liquid and/or semi-solid stool. The second membrane portion 162 acts as a mounting interface between the support wall 28 and the first membrane portion 160. The second portion 162 is welded (e.g. at 163) to the support wall 28, and extends outside the periphery of the support wall 28 (for example by a small distance less than 10 mm, preferably of the order of or less than 5 mm). The first membrane portion 160 is welded to the second membrane portion 162 outside the periphery of the support wall 28. This provides convenient technique for mounting the membrane portion 162, which might otherwise require a complicated or intricate welding operation if welded directly to the support wall 28. It also allows for increased separation between the point of welding of the first membrane portion 160 and the edge of the resilient foam 26 placed inside the seal chamber 30 prior to welding, thereby reducing risk of welding damage to the foam 26 or to the vertical surface of the first membrane portion 160. The second membrane portion 162 includes one or more cut-outs 161 for permitting the ports 32a and 32b to communicate with the interior of the seal chamber 30.

The seal support wall 28 carries the ports 32a and 32b for controlling the flow of fluid into and/or out of the stoma seal 16. The port 32a is defined by a tube or chimney 166 projecting from the support wall 28. The chimney 166 contains a pad of flow restricting material, such as microporous material 168, that is held in the chimney 166 by an interference fit. The port 32b is comprised of an umbrella valve 170 or other pressure relief valve, mounted on the upper surface of the support wall 28. The umbrella valve 170 is made of resilient flexible material, and has the form of an open umbrella or mushroom. The valve is normally biased to bear against and seal a port aperture in the support wall 28. When the pressure under the valve 170 exceeds the pressure relief threshold, the pressure overcomes the bias and lifts the valve out of sealing engagement to open discharge flow. The resilient nature of the valve 170 recloses the port aperture when the pressure drops below the threshold. The umbrella valve 170 is partly surrounded and protected by one or more spacer upstands or vertical ribs 172.

The third module 150 is locatable, and assemble to the first module 130, in an operative position at least partly within in the chamber 138 of the first module 130. In the operative position, the seal support wall 28 is arranged close to the top wall 14a, leaving a channel therebetween for venting of flatus. A shaped piece of open-cell foam 176 may be disposed in the channel between the seal support wall 28 and the top wall 14a. The open-cell foam 176 may act as a phase separator for protecting the filter 20 from contamination by any liquid or semi-solid stool that might leak undesirably past the stoma seal 16. The pores or cells of the foam tend to trap, or resist entry or passage of, liquid and semi-solid stool, while permitting gas to pass relatively unobstructed. The space communicates with the chamber 138 around an annular gap 178 between the periphery of the support wall 28 and the waste collector 116. In use, flatus gas that the stoma seal 16 allows to pass into the chamber 138 enters the channel via the annular gap 178. The flatus passes through the open-cell foam, and then through the deodorising filter 20, and into the outlet plenum 154 before venting to atmosphere via the outlet apertures 22.

The foam piece 176 is shaped with recesses 180 at positions to fit around the chimney 166, and around the umbrella valve 170 and its spacer upstands 172. The chimney 166 passes through a socket aperture 182 in the support wall 28 such that the first port 32a can communicate directly with external atmosphere. In contrast, the second port 32b communicates with the vent channel that is covered by the top wall 14a. Such an arrangement protects the pressure relief umbrella valve 170 from possible accidental external interference or blockage, ensuring that the valve 170 can always function as intended to allow at least some inflation fluid to escape from the seal chamber 30 if the pressure is too high. The spacer upstands 172 act as a guard fence partly around the valve 170 preventing the edge of the foam piece 176 from interfering with the valve 170. Additionally or alternatively, the spacer upstands 172 function to ensure that, at least in the region of the valve 170, the support wall 28 is always spaced from the top wall 14a by a spacing at least equal to the height of the upstands 172, thereby providing sufficient clearance height for the umbrella valve 170 to lift and open when appropriate. Any inflation fluid discharging through the valve 170 into the channel can vent to atmosphere through the filter 20 in the same manner as flatus.

The first module 130 and the third module 150 are mechanically coupled together in the assembled condition by an interference fit between (i) interlocking retainers 184 on the support wall 28 and the top wall 14a, and/or (ii) the chimney 166 received in the socket 182.

In the second module 140, the central aperture 186 around which the skirt 14b extends may be circular or non-circular. In the present embodiment, the aperture 186 is frusto-circular, having one side covered by a panel portion 188. The panel portion 188 includes a second socket aperture 190 for receiving the tip of the chimney 166 projecting through the first socket aperture 182. The top wall 14a of the first module 130 may have a generally planar upper surface, but in the preferred embodiment, the top wall 14a has a stepped upper surface, including a slightly proud portion 192. The proud portion 192 has a shape to match the frusto-circular shape of the aperture 186 such that, when the second module 140 is assembled around the first module 130, the proud portion 192 fits within the aperture 186, and is substantially planar with the panel 188. The top wall 14a and the skirt 14b thus form an integral-like assembly, with a flat upper surface. The second module 140 and the first module 130 are mechanically coupled together in the assembled condition by a mechanical interference fit between (i) the chimney 166 of the second module 150 assembled to the first module 130 and projecting through the second socket aperture 190, and/or (ii) inter-fitting retainer formations (not shown) around portions of the periphery of the proud portion 192 of the top wall 14a, and the periphery of the aperture 186 of the skirt 14b.

The frangible portion 114 is associated with the lift-to-open tab 200 integrated into the skirt 14b. The tab 200 is delimited on either side by grooves 202 in the skirt 14b. The frangible portion 114 is implemented at at least one of the grooves 202. In normal use of the appliance 10, the lift-to-open tab 200 forms part of the closed loop shape of the skirt 14b. Later, when the user desires to float the cover 14 from the first member 18, the user applies finger pressure to manipulate the tab 200. Manipulation of the tab 200 distorts the plastics material of the skirt 14b as the tab 200 is bent upwardly. The manipulation tears through the frangible portion 114, splitting the closed loop shape of the skirt 14b to form a split (not closed) loop. Splitting the skirt 14b removes the bracing effect of the bracing portion 80, thereby allowing the cover 14 to float free of the first member 18, while remaining captive to the first member 18 by the waste collector 116. The portions that float free as an integral assembly include one or more of: the split skirt 14b, the top wall 14a, the seal support wall 28, and the seal 16.

Figure 16:
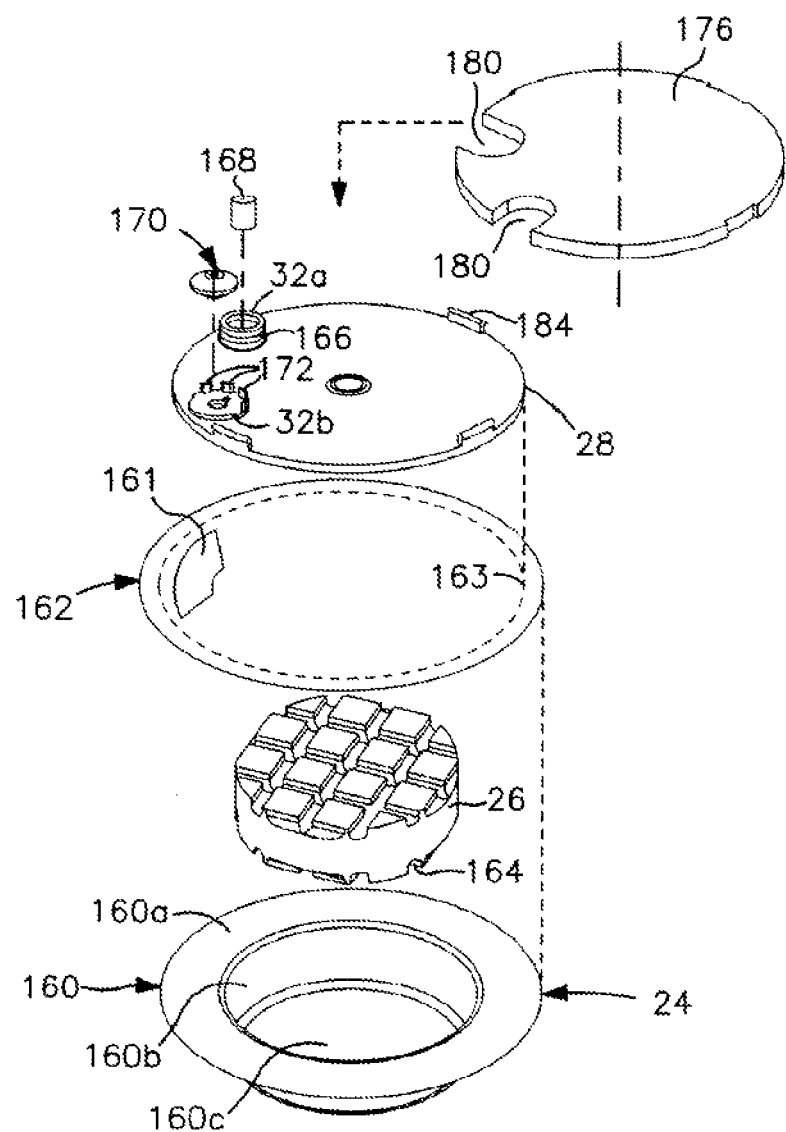
FIG. 16 is a schematic exploded view illustrating the components of the third module.

To produce the appliance 10, the modules 130, 140 and 150 are assembled in any order as desired. During assembly, the foam piece 176 is arranged between the top wall 14a and the seal support wall 28. The foam piece 176 might not be an integral part of any individual module (although it is shown in FIG. 16 associated with the third module 150 for ease of understanding). The foam piece 176 is retained captive once the modules are assembled together. Also during assembly, the waste collector 116 is collapsed down to its stowed form, in which the waste collector 116 is tightly accommodated in the space just radially inside the bracing portion 80.

It will be appreciated that the modular construction of the appliance 10 can enable a complicated and compact ostomy appliance to be produced economically and reliably. Each module 130, 140, 150 is relatively straightforward to manufacture as an individual item. The relatively complicated appliance is then produced by assembling the modules together.

It will also be appreciated that the foregoing description is merely illustrative of a preferred embodiment of the invention, and does not limit the invention. Many alternatives, equivalents and improvements may be made within the scope and/or spirit of the invention.

The invention claimed is:

1. A controlled discharge ostomy appliance assembly comprising:
   (a) a controlled discharge ostomy appliance having a body-facing side and comprising:
      a cover;
      a body fitment;
      a stoma seal disposed within the cover, and
      a first coupling member configured for coupling to the body fitment configured for mounting the controlled discharge ostomy appliance in an operative position at a stoma, the first coupling member being displaceable with respect to the cover from an unlocked position to a locked position; and
   (b) a protector shield configured for protecting the body-facing side of the controlled discharge ostomy appliance, the protector being made of integrally molded plastics and comprising:
      a substantially rigid coupling member guard portion configured for protecting the first coupling member of the controlled discharge ostomy appliance from external forces capable of displacing the first coupling member from the unlocked position to the locked position, and
      a fastener configured for co-operating with the controlled discharge ostomy appliance at a location distinct from the first coupling member, to fasten the protector to the controlled discharge ostomy appliance releasably to form a combined assembly therewith.

2. The controlled discharge ostomy assembly of claim 1, wherein the protector shield further comprises a seal displacer configured for displacing the stoma seal from a deployed position to a non-deployed position.

3. The controlled discharge ostomy assembly of claim 1, wherein:
   (a) the controlled discharge ostomy appliance further comprises a second coupling member including a frangible portion that is breakable or tearable in use for releasing the controlled discharge ostomy appliance from the body fitment; and
   (b) the protector shield further comprises
      a bracing portion for bracing and supporting the second coupling member of the controlled discharge ostomy appliance, to prevent tearing of the frangible portion prior to first use.

4. A controlled discharge ostomy appliance assembly comprising:
   (a) a controlled discharge ostomy appliance having a body-facing side and comprising:
      a stoma seal, and
      a member including a frangible portion that is breakable or tearable in use configured for releasing at least one of (i) the stoma seal from an operative position; and (ii) the controlled discharge ostomy appliance from a body fitment; and
   (b) a protector shield configured for protecting the body-facing side of the controlled discharge ostomy appliance, the protector being made of integrally molded plastics and comprising:
      a bracing portion configured for bracing and supporting said member of the controlled discharge ostomy appliance, to prevent tearing of the frangible portion prior to first use, and
      a fastener configured for co-operating with the controlled discharge ostomy appliance, to fasten the protector to the controlled discharge ostomy appliance to form a combined assembly therewith.

5. The controlled discharge ostomy assembly of claim 4, wherein the protector shield further comprises a seal displacer configured for displacing the seal of the controlled discharge ostomy appliance from a deployed position to a non-deployed position.

6. A protector shield for protecting a body-facing side of a controlled discharge ostomy appliance, the protector shield being made of integrally molded plastics and comprising:
   (i) a protector;
   (ii) a seal displacer configured for displacing a self-urging seal of the controlled discharge ostomy appliance from a deployed position to a non-deployed position,
   (iii) a substantially rigid coupling member guard portion configured for protecting a first coupling member of the controlled discharge ostomy appliance from external forces capable of displacing the first coupling member from an unlocked position to a locked position,
   (iv) a bracing portion configured for bracing and supporting a second coupling member of the controlled discharge ostomy appliance, the second coupling member including a frangible portion that is breakable or tearable in use to release the controlled discharge ostomy appliance, and
   (v) a fastener configured for co-operating with a periphery of the controlled discharge ostomy appliance, to releasably fasten the protector shield to the controlled discharge ostomy appliance to form a combined assembly therewith.

7. The protector shield of claim 6, wherein the seal displacer is located at a centre of the protector.

8. The protector shield of claim 6, wherein the coupling member guard portion comprises a channel shaped fender, the fender extending in a closed loop to define an endless channel.

9. The protector shield of claim 6, wherein the coupling member guard portion extends around the seal displacer.

10. The protector shield of claim 9, wherein the seal displacer and the coupling member guard portion adjoin at a bendable interface portion.

11. The protector shield of claim 6, wherein the bracing portion comprises a step-shaped recess extending around a closed loop shaped path.

12. The protector shield of claim 6, wherein the fastener comprises at least one undercut lug.